United States Patent [19]

Patsch et al.

[11] 4,164,500
[45] Aug. 14, 1979

[54] PYRAZOLINE COMPOUNDS

[75] Inventors: Manfred Patsch; Albert Hettche, both of Ludwigshafen, Fed. Rep. of Germany

[73] Assignee: BASF Aktiengesellschaft, Fed. Rep. of Germany

[21] Appl. No.: 898,629

[22] Filed: Apr. 21, 1978

Related U.S. Application Data

[62] Division of Ser. No. 702,975, Jul. 6, 1976, Pat. No. 4,129,563.

[30] Foreign Application Priority Data

Jul. 31, 1975 [DE] Fed. Rep. of Germany ....... 2534180
Aug. 6, 1975 [DE] Fed. Rep. of Germany ....... 2535095
Nov. 11, 1975 [DE] Fed. Rep. of Germany ....... 2550548

[51] Int. Cl.² ........................................... C07D 231/06
[52] U.S. Cl. ................................................ 260/239.9
[58] Field of Search ..................................... 260/239.9

[56] References Cited

U.S. PATENT DOCUMENTS 3,988,346  10/1976  Schmid .............................. 260/239.9

*Primary Examiner*—Natalie Trousof
*Assistant Examiner*—Jane T. Fan
*Attorney, Agent, or Firm*—Keil & Witherspoon

[57] ABSTRACT

Pyrazoline compounds of the formula (I):

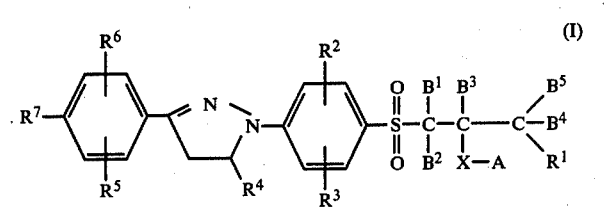

in which
each of
  $B^1$ to $B^5$ is hydrogen or $C_1$ to $C_4$ alkyl;
  $R^1$ is hydrogen, alkyl or hydroxy;
  $R^2$, $R^3$, $R^5$, $R^6$ and $R^7$ independently of one another are hydrogen, chloro, bromo, fluoro, methyl, ethyl, methoxy or ethoxy;
  $R^4$ is hydrogen, alkyl, benzyl, phenylethyl or also phenyl optionally bearing chloro, bromo, methyl, ethyl, methoxy, ethoxy, cyano, dialkylamino or $SO_3H$ as a substituent;
  X is $-O-$, $-S-$, $-NR^8-$, $-NR^8CO-$, $-NR^8-SO_2-$, $-OSO_3-$ or $-SO_3-$;
  $R^8$ is hydrogen, alkyl or alkyl bearing hydroxy or $C_1$ to $C_4$ alkoxy as a substituent;
  A is hydrogen, sodium, potassium, unsubstituted or substituted ammonium, unsubstituted or substituted alkyl, cycloalkyl, aralkyl or aryl; and
  $-NR^8-$ and A together may be an optionally quaternized saturated or unsaturated heterocyclic ring.

The compounds are eminently suitable as optical brighteners for example for acrylonitrile polymers, wool and polyamides.

3 Claims, No Drawings

PYRAZOLINE COMPOUNDS

This application is a division of Ser. No. 702,975 filed July 6, 1976, now issued as U.S. Pat. No. 4,129,563, on Dec. 12, 1978.

The invention relates to compounds of the general formula (I):

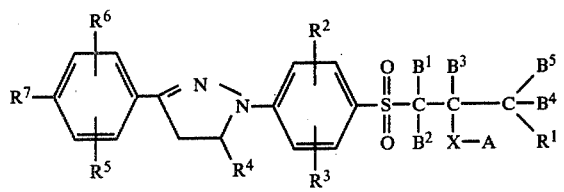

in which
- $B^1$ to $B^5$ are each hydrogen or $C_1$ to $C_4$ alkyl;
- $R^1$ is hydrogen, alkyl or hydroxy;
- $R^2$, $R^3$, $R^5$, $R^6$ and $R^7$ independently of one another are hydrogen, chloro, bromo, fluoro, methyl, ethyl, methoxy or ethoxy;
- $R^4$ is hydrogen, alkyl, benzyl, phenylethyl, phenyl or phenyl bearing chloro, bromo, methyl, ethyl, methoxy, ethoxy, cyano, dialkylamino or $SO_3H$ as a substituent;
- X is —O—, —S—, —$NR^3$—, —$NR^8CO$—, —$NR^8SO_2$—, —$OSO_3$— or —$SO_3$—;
- $R^8$ is hydrogen, alkyl or alkyl bearing hydroxy or $C_1$ to $C_4$ alkoxy as a substituent;
- A is hydrogen, sodium, potassium, ammonium, substituted ammonium or unsubstituted or substituted alkyl, cycloalkyl, aralkyl or aryl; and
- —$NR^8$— and A together are an optionally quaternized saturated or unsaturated heterocyclic ring.

Examples of dialkylaminophenyl radicals $R^4$ are $C_1$ to $C_4$ dialkylaminophenyl such as dimethylaminophenyl, diethylaminophenyl or dibutylaminophenyl.

Examples of alkyl radicals $R^1$, $R^4$ and $R^8$ are those of one to six carbon atoms such as hexyl, amyl, butyl or propyl and particularly methyl or ethyl. Radicals $R^8$ may also be β-hydroxyethyl, β-methoxyethyl, β-ethoxyethyl, β-propoxyethyl, β-butoxyethyl, β-methoxypropyl, β-ethoxypropyl, β-propoxypropyl or β-butoxypropyl. Examples of alkyl radicals $B^1$ to $B^5$ are butyl, propyl, ethyl and methyl. $B^1$ to $B^5$ are preferably hydrogen or methyl. Radicals A may be hydrogen or for example $C_1$ to $C_{13}$ alkyl which may be interrupted by oxygen or sulfur and may bear, as substituent, hydroxy, $C_1$ to $C_4$ alkoxy, phenoxy, cyano, chloro, bromo, carboxy, carbomethoxy, carboethoxy, carbobutoxy, carbamoyl, N-alkylcarbamoyl (alkyl being $C_1$ to $C_6$), $SO_3H$, amino, $C_1$ to $C_8$ alkylamino or dialkylamino, pyrrolidino, piperidino, hexamethylene amino, morpholino, piperazino, N-methylpiperazino, N-β-hydroxyethylpiperazino, quaternary ammonium or cyclic ammonium. In one claimed embodiment $R^2$, $R^3$, $R^4$, $R^5$, $R^6$ and $B^3$ are hydrogen. In another claimed embodiment $R^2$, $R^3$, $R^4$, $R^5$, $R^6$ and $B^3$ are hydrogen and $R^7$ is chlorine.

The following specific radicals A are given by way of example: $CH_3$, $C_2H_5$, $C_3H_7$, $C_4H_9$, $C_5H_{11}$, $C_6H_{13}$, $C_7H_{15}$, $C_8H_{17}$, $C_9H_{19}$, $C_{10}H_{21}$ $C_{13}H_{27}$, $C_2H_4OH$, $C_3H_6OH$,

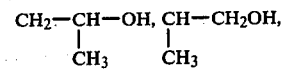

$C_4H_8OH$, $C_6H_{12}OH$, $C_2H_4OC_2H_4OH$, $C_3H_6OC_2H_4OH$, $C_2H_4OCH_3$, $C_3H_6OCH_3$, $C_4H_8OCH_3$, $C_6H_{12}OCH_3$, $C_2H_4OC_2H_5$, $C_3H_6OC_2H_5$, $C_4H_8OC_2H_5$, $C_2H_4OC_3H_7$, $C_3H_6OC_3H_7$, $C_2H_4OC_4H_9$, $C_3H_6OC_4H_9$, $C_3H_6OC_8H_{17}$, $C_2H_4OC_6H_5$, $C_3H_6OC_6H_5$, $C_2H_4OC_2H_4OCH_3$, $C_2H_4OC_2H_4OC_2H_5$, $C_2H_4(OC_2H_4)_2OCH_3$, $C_2H_4OC_2H_4OC_6H_5$, $C_2H_4(OC_2H_4)_2OC_2H_5$, $C_2H_4SCH_3$, $C_2H_4SC_2H_5$, $C_2H_4SC_4H_9$, $C_2H_4S$—$CH_2$—$C_6H_5$, $C_2H_4CN$, $C_5H_{10}CN$, $C_6H_{12}CN$, $C_7H_{14}CN$, $C_2H_4OC_2H_4CN$, $C_2H_4OC_2H_4CN$, $C_3H_6OC_2H_4CN$, $C_2H_4Cl$, $C_3H_6Cl$, $C_4H_8Cl$, $C_6H_{12}Cl$, $C_2H_4Br$, $C_3H_6Br$, $C_2H_4SO_3H$, $CH_2COOH$, $CH_2$—$COOCH_3$, $C_2H_4COOH$, $C_2H_4COOC_2H_5$, $C_2H_4COOC_4H_9$, $C_2H_4CONHC_4H_9$, $C_2H_4CONHCH_3$, $C_2H_4CONHC_2H_5$, $C_2H_4CONHC_6H_{13}$,

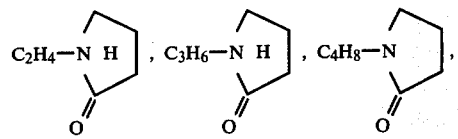

$C_2H_4NH_2$, $C_2H_4NH$—$CH_3$, $C_3H_6NHC_2H_5$, $C_3H_6NHC_3H_7$, $C_2H_4NHC_4H_9$,

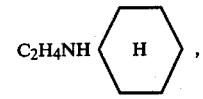

$C_3H_6NHC_6H_{13}$, $C_3H_6NHC_8H_{17}$, $C_2H_4N(CH_3)_2$, $C_2H_4N(C_2H_5)_2$, $C_2H_4N(C_3H_7)_2$, $C_2H_4N(C_4H_9)_2$, $C_2H_4N(C_5H_{11})_2$, $C_2H_4N(C_6H_{13})_2$,

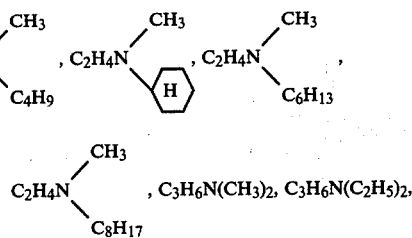

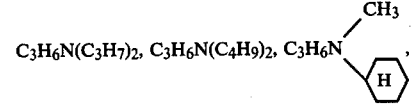

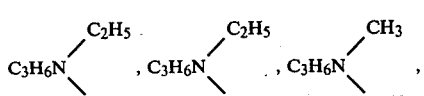

$C_4H_8N(CH_3)_2$, $C_4H_8N(C_2H_5)_2$, $C_4H_8N(C_4H_9)_2$,

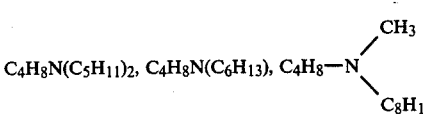

-continued $C_4H_8N\begin{smallmatrix}CH_3\\C_4H_9\end{smallmatrix}$, $C_4H_8N\begin{smallmatrix}C_2H_5\\C_3H_7\end{smallmatrix}$, $C_6H_{12}N(CH_3)_2$, $C_6H_{12}N(C_2H_5)_2$, $C_6H_{12}N(C_4H_9)_2$, $C_6H_{12}N(C_6H_{13})_2$, $C_6H_{12}N\begin{smallmatrix}CH_3\\C_4H_9\end{smallmatrix}$, $C_6H_{12}N\begin{smallmatrix}CH_3\\C_8H_{17}\end{smallmatrix}$, $CH_2-CH-N(CH_3)_2$
                                                                          $\ \ \ \ \ \ \ \ \ \ |$
                                                                          $\ \ \ \ \ \ \ \ \ CH_3$ $CH_2-CH-N(C_2H_5)_2$, $CH_2-CH-N(C_3H_7)_2$,
$\ \ \ \ \ \ \ |$                  $\ \ \ \ \ \ \ |$
$\ \ \ \ \ CH_3$                 $\ \ \ \ CH_3$ $CH_2-CH-N(C_4H_9)_2$,
$\ \ \ \ \ \ \ |$
$\ \ \ \ \ CH_3$ $CH_2-CH-N(C_5H_{11})_2$, $CH_2-CH-N\begin{smallmatrix}CH_3\\C_4H_9\end{smallmatrix}$,
$\ \ \ \ \ \ \ |$                      $\ \ \ \ \ \ \ |$
$\ \ \ \ \ CH_3$                     $\ \ \ \ CH_3$ $CH_2-CH-N\begin{smallmatrix}C_2H_5\\C_4H_9\end{smallmatrix}$,
$\ \ \ \ \ \ \ |$
$\ \ \ \ \ CH_3$ $CH_2-CH-N\begin{smallmatrix}C_3H_7\\C_5H_{11}\end{smallmatrix}$, $CH_2-CH-N\begin{smallmatrix}C_4H_9\\C_8H_{17}\end{smallmatrix}$,
$\ \ \ \ \ \ \ |$                          $\ \ \ \ \ \ \ |$
$\ \ \ \ \ CH_3$                        $\ \ \ \ CH_3$ $CH_2-CH-N\begin{smallmatrix}CH_3\\C_6H_5\end{smallmatrix}$, $CH_2-CH-N\begin{smallmatrix}CH_3\\C_6H_5\end{smallmatrix}$,
$\ \ \ \ \ \ \ |$                          $\ \ \ \ \ \ \ |$
$\ \ \ \ \ CH_3$                        $\ \ \ \ CH_3$ $CH_3$                   $CH_3$
$\ |$                      $\ |$
$CH-CH_2-N\begin{smallmatrix}CH_3\\CH_3\end{smallmatrix}$, $CH-CH_2-N\begin{smallmatrix}C_2H_5\\C_2H_5\end{smallmatrix}$, $CH_3$                   $CH_3$
$\ |$                      $\ |$
$CH-CH_2-N\begin{smallmatrix}C_3H_7\\C_3H_7\end{smallmatrix}$, $CH-CH_2-N\begin{smallmatrix}C_4H_9\\C_4H_9\end{smallmatrix}$, $CH_3$                   $CH_3$
$\ |$                      $\ |$
$CH-CH_2-N(C_5H_{11})_2$, $CH-CH_2-N(C_6H_{13})_2$, $CH_3$                   $CH_3$
$\ |$                      $\ |$
$CH-CH_2-N(C_8H_{17})_2$, $CH-CH_2-N\begin{smallmatrix}CH_3\\C_2H_5\end{smallmatrix}$, $CH_3$                   $CH_3$
$\ |$                      $\ |$
$CH-CH_2-N\begin{smallmatrix}CH_3\\C_8H_{17}\end{smallmatrix}$, $CH-CH_2-N\begin{smallmatrix}CH_3\\C_4H_9\end{smallmatrix}$, $CH_3$                   $CH_3$
$\ |$                      $\ |$
$CH-CH_2N\begin{smallmatrix}C_2H_5\\C_8H_{17}\end{smallmatrix}$, $CH-CH_2-N\begin{smallmatrix}C_2H_5\\C_4H_9\end{smallmatrix}$, $C_2H_5$                   $CH_3$
$\ \ |$                      $\ |$
$CH-CH_2-N(CH_3)_2$, $CH-CH_2-N(C_2H_5)_2$, $C_2H_5$                   $C_2H_5$
$\ \ |$                      $\ \ |$
$CH-CH_2-N(C_5H_7)_2$, $CH-CH_2-N(C_4H_9)_2$, -continued $C_2H_5$                   $C_2H_5$
$\ \ |$                      $\ \ |$
$CH-CH_2-N(C_6H_{13})_2$, $CH-CH_2-N(C_8H_{17})_2$, $C_2H_5$                   $C_2H_5$
$\ \ |$                      $\ \ |$
$CH-CH_2-N\begin{smallmatrix}CH_3\\C_2H_5\end{smallmatrix}$, $CH-CH_2-N\begin{smallmatrix}C_3H_7\\C_4H_9\end{smallmatrix}$, $\ \ \ \ \ CH_3$                 $\ \ \ \ \ CH_3$
$\ \ \ \ \ \ |$                      $\ \ \ \ \ \ |$
$CH_2-C-CH_2-N(CH_3)_2$, $CH_2-C-CH_2N(C_2H_5)_2$,
$\ \ \ \ \ \ |$                      $\ \ \ \ \ \ |$
$\ \ \ \ \ CH_3$                 $\ \ \ \ \ CH_3$ $\ \ \ \ \ CH_3$                 $\ \ \ \ \ CH_3$
$\ \ \ \ \ \ |$                      $\ \ \ \ \ \ |$
$CH_2-C-CH_2-N(C_4H_9)_2$, $CH_2-C-C_2N\begin{smallmatrix}CH_3\\C_3H_7\end{smallmatrix}$,
$\ \ \ \ \ \ |$                      $\ \ \ \ \ \ |$
$\ \ \ \ \ CH_3$                 $\ \ \ \ \ CH_3$ $\ \ \ \ \ CH_3$                 $\ \ \ \ \ CH_3$
$\ \ \ \ \ \ |$                      $\ \ \ \ \ \ |$
$CH_2-C-CH_2-N\begin{smallmatrix}CH_3\\C_4H_9\end{smallmatrix}$, $CH_2-C-CH_2-N\begin{smallmatrix}CH_3\\C_8H_{17}\end{smallmatrix}$,
$\ \ \ \ \ \ |$                      $\ \ \ \ \ \ |$
$\ \ \ \ \ CH_3$                 $\ \ \ \ \ CH_3$ $C_3H_7$                   $C_4H_9$
$\ \ |$                      $\ \ |$
$CH-CH_2-N(C_2H_5)_2$, $CH-CH_2-N(C_4H_9)_2$, $C_5H_{11}$                   $C_6H_{13}$
$\ \ |$                      $\ \ |$
$CH-CH_2-N(C_2H_5)_2$, $CH-CH_2-N(C_4H_9)_2$, $C_2H_4N\overset{\frown}{\underset{\smile}{H}}$, $C_3H_6N\overset{\frown}{\underset{\smile}{H}}$, $C_4H_8N\overset{\frown}{\underset{\smile}{H}}$, $C_5H_{10}N\overset{\frown}{\underset{\smile}{H}}$, $CH-CH_2-N\overset{\frown}{\underset{\smile}{H}}$, $CH_2-CH-N\overset{\frown}{\underset{\smile}{H}}$,
$\ \ \ \ \ \ \ \ \ \ \ \ \ \ \ \ \ |$                      $\ \ \ \ \ \ \ \ \ \ \ \ \ \ \ \ |$
$\ \ \ \ \ \ \ \ \ \ \ \ \ CH_3$                 $\ \ \ \ \ \ \ \ \ \ \ \ CH_3$ $C_2H_5$                          $\ \ \ \ CH_3$
$\ \ |$                             $\ \ \ \ \ |$
$CH-CH_2-N\overset{\frown}{\underset{\smile}{H}}$, $CH_2-C-CH_2-N\overset{\frown}{\underset{\smile}{H}}$,
                                  $\ \ \ \ \ |$
                                  $\ \ \ CH_3$ $C_2H_4N\overset{\frown}{\underset{\smile}{\ H\ }}$, $C_3H_6-\overset{\frown}{\underset{\smile}{N\ H\ }}$, $C_4H_8N\overset{\frown}{\underset{\smile}{\ H\ }}$, $\ \ \ CH_3$                   $\ \ \ CH_3$
$\ \ \ \ |$                      $\ \ \ \ |$
$CH_2-CH-N\overset{\frown}{\underset{\smile}{\ H\ }}$, $CH-CH_2-N\overset{\frown}{\underset{\smile}{\ H\ }}$, $C_2H_5$
$\ \ |$
$CH-CH_2-N\overset{\frown}{\underset{\smile}{\ H\ }}$, $\ \ \ \ CH_3$
$\ \ \ \ \ |$
$CH_2-C-CH_2-N\overset{\frown}{\underset{\smile}{\ H\ }}$, $C_2H_4-N\overset{\frown}{\underset{\smile}{\ H\ }}$,
$\ \ \ \ \ |$
$\ \ \ CH_3$ $C_3H_6N\overset{\frown}{\underset{\smile}{\ H\ }}$,

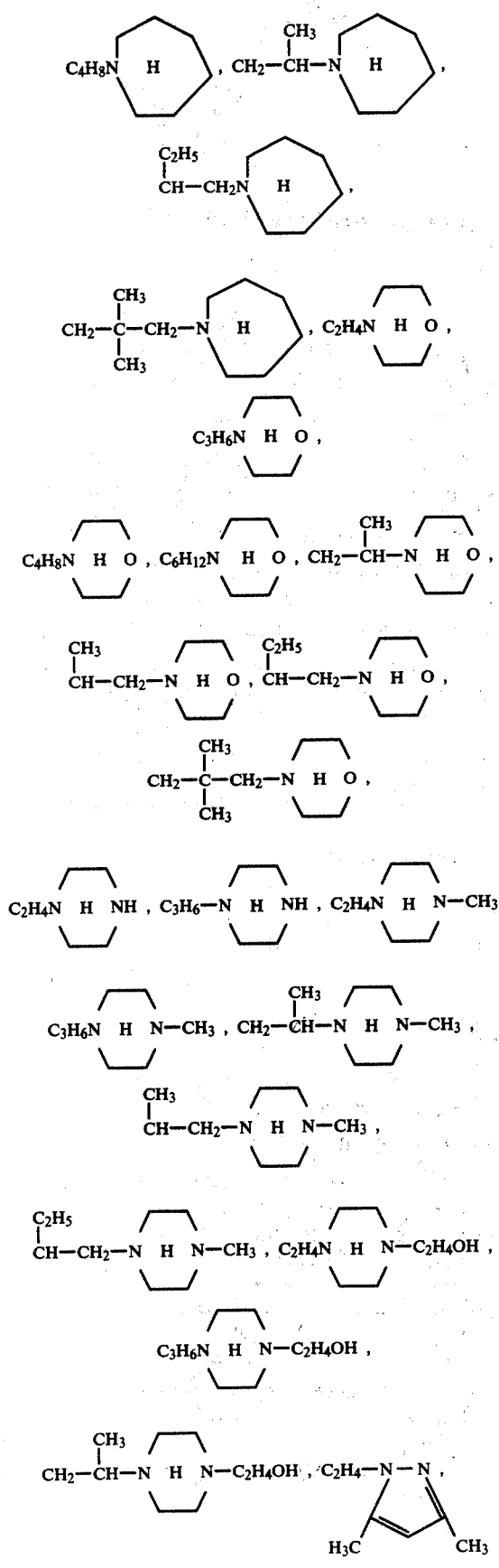

-continued
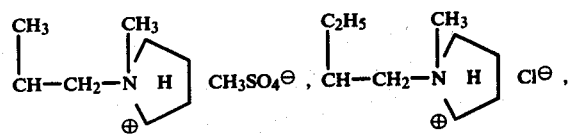
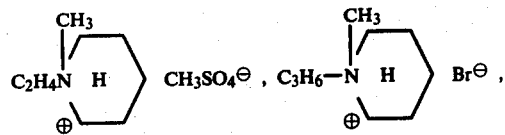
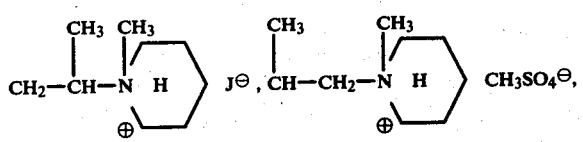
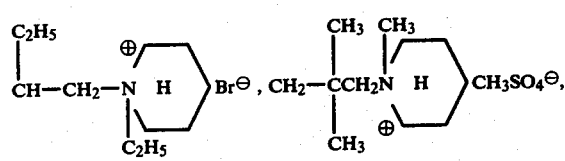
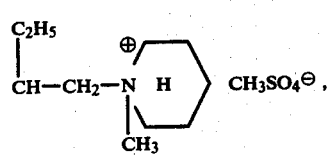
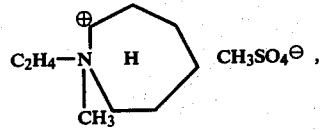
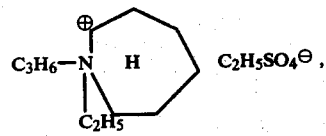
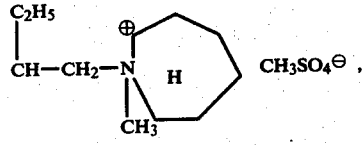
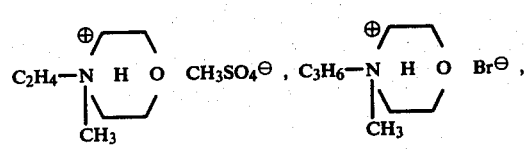
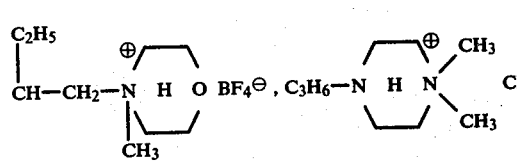
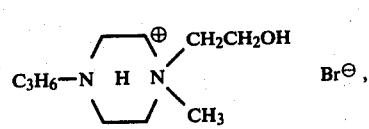
-continued
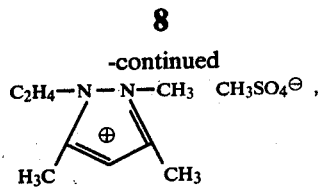
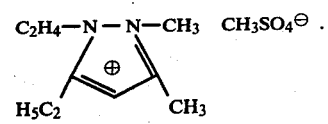
Cycloalkyl, aralkyl or aryl radicals A are for example:
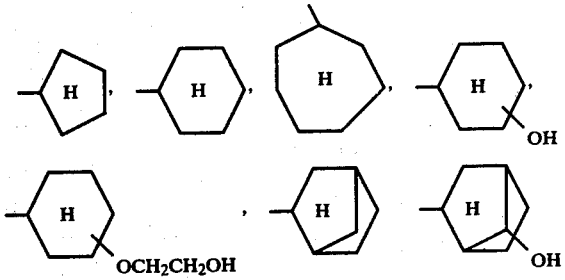
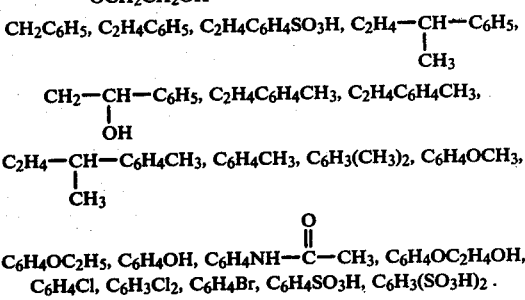
$CH_2C_6H_5$, $C_2H_4C_6H_5$, $C_2H_4C_6H_4SO_3H$, $C_2H_4-CH-C_6H_5$,
                                                         $|$
                                                        $CH_3$
$CH_2-CH-C_6H_5$, $C_2H_4C_6H_4CH_3$, $C_2H_4C_6H_4CH_3$,
       $|$
      $OH$
$C_2H_4-CH-C_6H_4CH_3$, $C_6H_4CH_3$, $C_6H_3(CH_3)_2$, $C_6H_4OCH_3$,
       $|$
      $CH_3$
$$C_6H_4OC_2H_5,\ C_6H_4OH,\ C_6H_4NH-\overset{O}{\underset{\|}{C}}-CH_3,\ C_6H_4OC_2H_4OH,$$
$C_6H_4Cl$, $C_6H_3Cl_2$, $C_6H_4Br$, $C_6H_4SO_3H$, $C_6H_3(SO_3H)_2$.
Examples of radicals
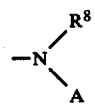
are:
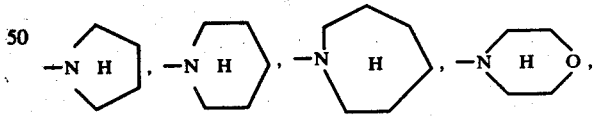
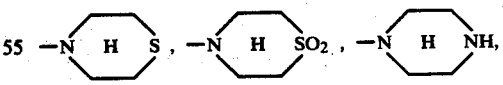
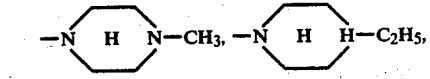
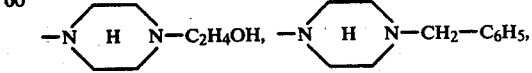
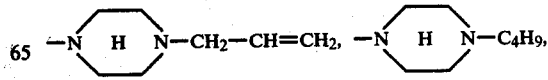

-continued

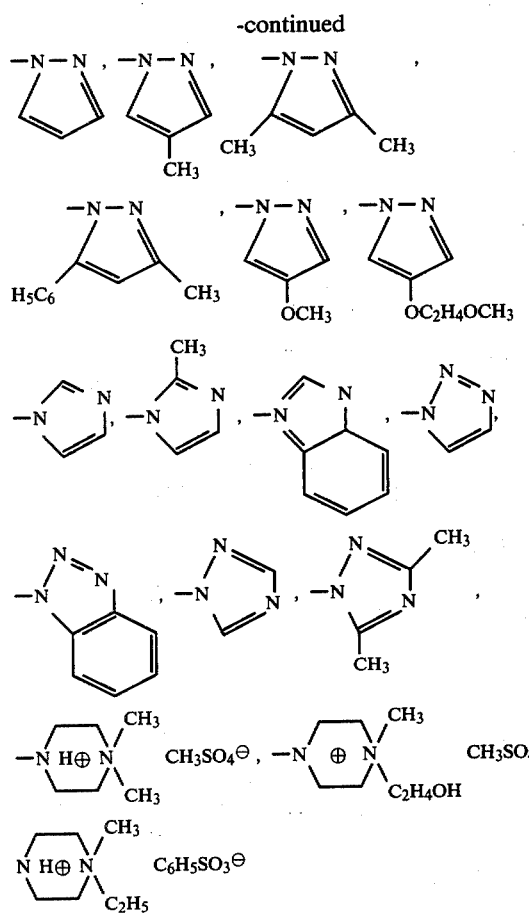

Compounds of the formula (I) may be prepared by reacting a compound of the general formula (II):

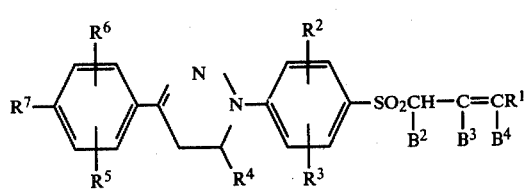

with a compound of the general formula (III):

H—X—A         (III)

in the presence of a base, X being —O—, —S—, —NR$^8$—, —NR$^8$CO—, —SO$_3$— or —NR$^8$SO$_2$—.

Compounds of the formula (II) may be obtained by reacting a compound of the general formula (IV) or (V):

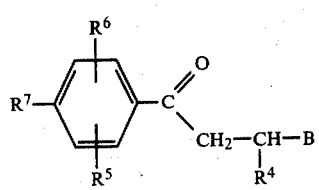

-continued

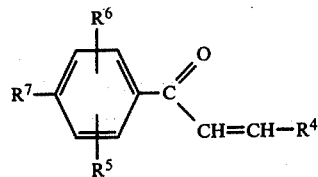

B being Cl, Br or dialkylamino, with a compound of the general formula (VI):

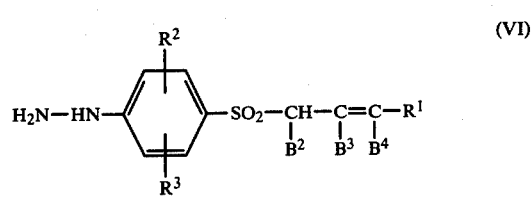

Compounds of the formula (VI) are accessible in the following way:

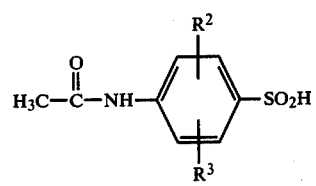

(1) alkylation
(2) hydrolysis

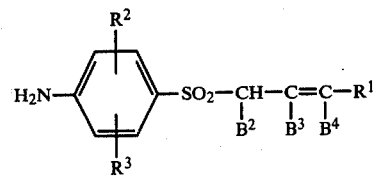

(1) diazotization
(2) reduction

Compounds of the formula (VI)

Compounds of the formula (I) in which X—A is OSO$_3$H may be obtained for example by reacting a compound of the general formula (I) in which X—A is OH with sulfuric acid.

Compounds of the formula (I) in which XA is SO$_3$Na may be obtained from compounds of the formula (I) in which XA is OSO$_3$Na or from (II) with an alkali metal sulfite, for example sodium sulfite.

Compounds of the formula (I) may also be prepared by the following method (B$^1$ to B$^5$ being shown as hydrogen for the sake of simplicity):

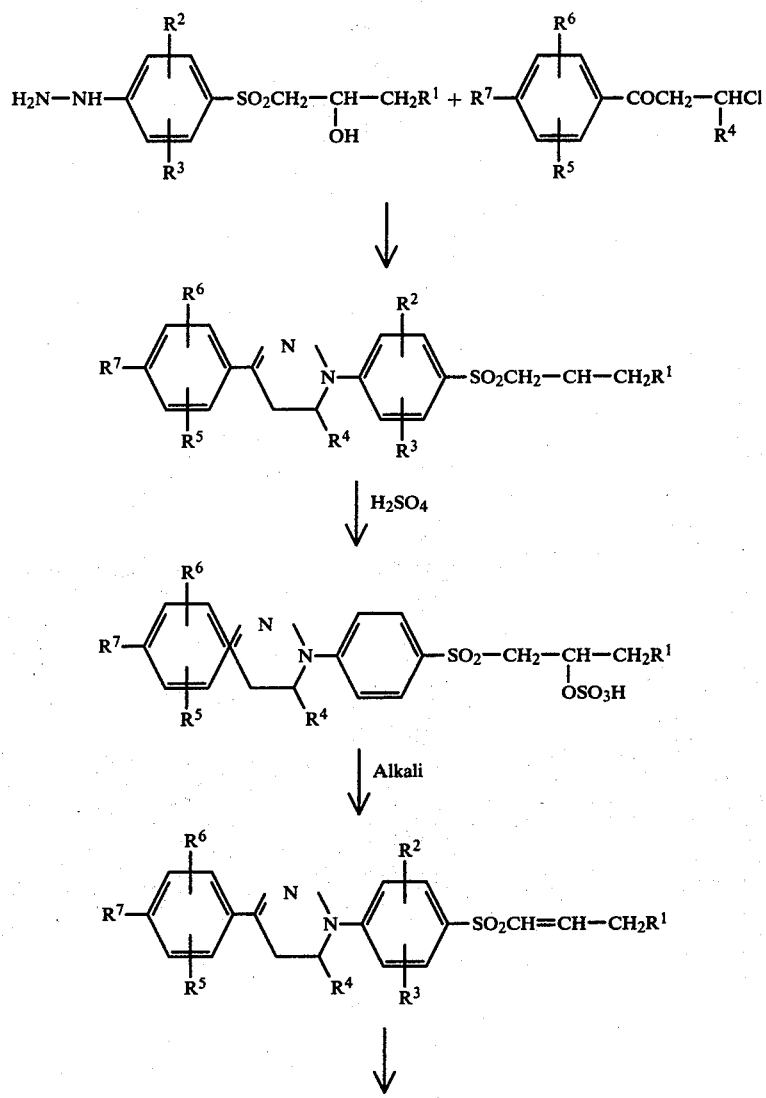

Compounds of the general formula (III)
Compounds of the general formula (I).
Compounds of the formula (I) may also be obtained by reacting a compound of the general formula (VIa):

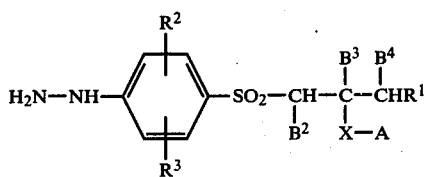

with a compound of the general formula (IV) or (V).
Compounds of the general formula (VIa) are accessible by the following method:

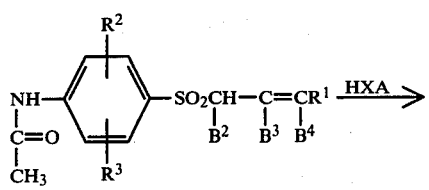

-continued

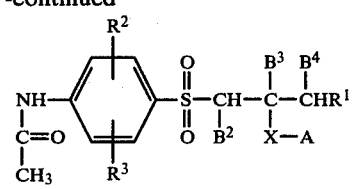

(1) Hydrolysis
(2) Diazotization
(3) Reduction

Compounds of the general formula (VIa)
Compounds (I) in which R¹ is OH may be obtained from a compound of the general formula (VII):

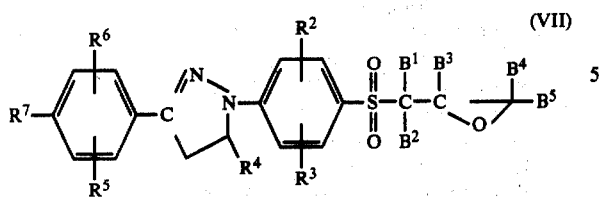 (VII)

with a compound of the formula (III).

Compounds of the formula (VII) may be obtained by reacting a compound of the formula (VIII):

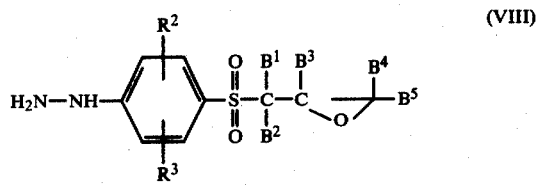 (VIII)

with a compound of the formula (IV) or (V).

Compounds of the formula (VIII) are accessible as follows:

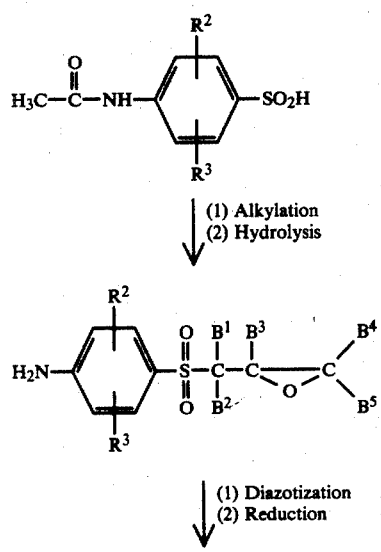

Compounds of the formula (VIII).

Compounds of the formula (I) in which $R^1$ is OH may also be obtained by reacting a compound of the formula (IX):

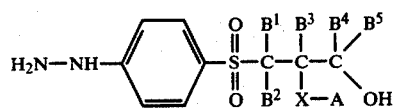

with a compound of the formula (IV) or (V).

Compounds of the general formula (IX) may be obtained as follows:

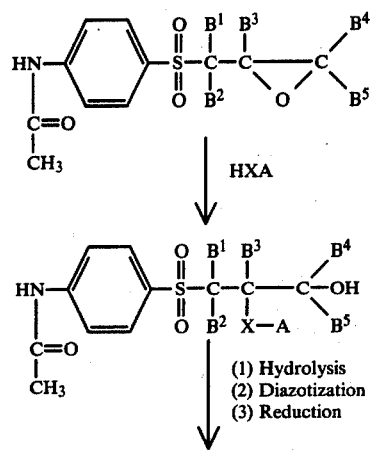

Compounds of the general formula (IX).

Compounds of the formula (I) in which $R^1$ is OH may furthermore be obtained by the reaction of a compound of the formula (with $B^1$ to $B^5$ represented as hydrogen for the sake of simplicity):

$$R^7\text{-}\underset{R^5}{\underset{|}{\bigcirc}}\text{-}\underset{R^4}{\underset{|}{C}}\text{-}\overset{R^6}{}\text{N}\diagdown\text{N}\text{-}\underset{R^3}{\underset{|}{\bigcirc}}\text{-}\text{SO}_2\text{CH}=\text{CH}-\text{CH}_2\text{OH}$$

or a precursor thereof of the formula:

$$R^7\text{-}\underset{R^5}{\underset{|}{\bigcirc}}\text{-}\underset{R^4}{\underset{|}{C}}\text{-}\overset{R^6}{}\text{N}\diagdown\text{N}\text{-}\underset{R^3}{\underset{|}{\bigcirc}}\text{-}\text{SO}_2\text{CH}_2-\underset{\underset{\text{OH}}{|}}{\text{CH}}-\text{CH}_2\text{Cl}$$

with a compound of the formula (III):

$$H-X-A \qquad (III).$$

Details concerning the reactions will be found in the Examples in which parts and percentages are by weight unless otherwise stated.

Particular industrial importance attaches to compounds of the general formula (Ia):

$$Cl\text{-}\bigcirc\text{-}\underset{}{\underset{}{C}}\text{-}\text{N}\diagdown\text{N}\text{-}\bigcirc\text{-}\text{SO}_2\text{CH}_2-\underset{\underset{X-A}{|}}{\text{CH}}-\underset{}{\overset{CH_2-R^1}{|}} \qquad (Ia)$$

in which $R^1$ is hydrogen or hydroxyl and XA has the meanings given above.

X is preferably —O—, —$NR^8$— or —$SO_3$— and A is preferably hydrogen, sodium, potassium, $C_1$ to $C_8$ alkyl, an amino group bearing one or two $C_1$ to $C_4$ alkyl as substituents, alkyl bearing the said heterocyclic rings as substituents and radicals containing quaternary nitrogen.

Preferred radicals are:

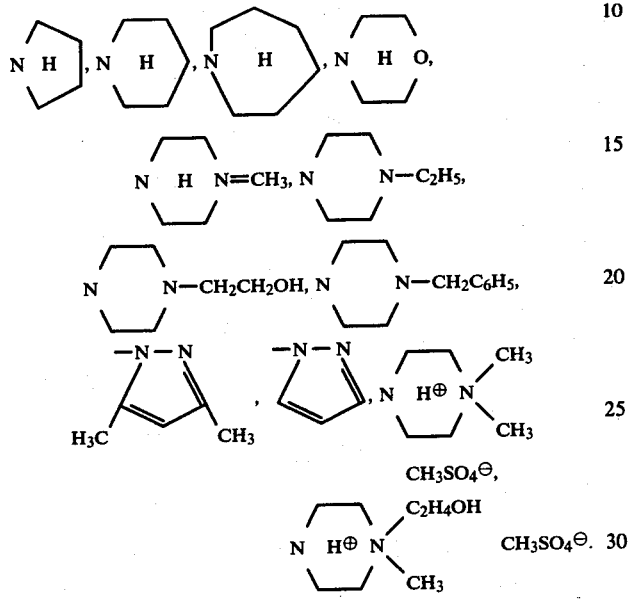

The compounds of the general formula (I) are suitable as optical brighteners for cellulose esters and particularly for acrylonitrile polymers, wool and polyamides. Brilliant white effects are obtained having good fastness properties and particularly high degrees of whiteness. The compounds of the formula (I) are moreover suitable for use in detergents for brightening paper. The main method of application is liquor dyeing.

The production of precursors

EXAMPLE A (a) 80 parts of p-acetylaminobenzenesulfinic acid is dissolved with 44 parts of sodium bicarbonate in 400 parts of water. 76 parts of epichlorohydrin is dripped in at 45° to 50° C. and the whole is stirred for another two hours at 45° to 50° C. It is then allowed to cool, the pH of the solution is adjusted to 11.5 by adding 30 parts of 50% by weight caustic soda solution, and 85 parts (83.5% of theory) of 4-acetylaminophenyl-3'-hydroxypropene-2'-sulfone having a melting point of 165° to 170° C. is isolated by suction filtration. The molecular weight (calculated and found) is 255.

NMR (D-DMSO): 2.1(S), 4.2(M), 5.2(T), 6.65(brD), 6.95(brD), 7.8(S), 10.3(brS), 3:2:1:1:1:4:1.

(b) 63.7 parts of 4-acetylamino-3'-hydroxypropene-2'-sulfone is heated for an hour at 100° C. in a mixture of 90 parts of water and 90 parts of concentrated hydrochloric acid. After the whole has been cooled to 0° to 5° C. diazotization is carried out with a solution of 17.3 parts of sodium nitrite in 50 parts of water. The diazonium solution is dripped into a solution of 188 parts of sodium sulfite in 550 parts of water, stirred for one hour at ambient temperature, 100 parts of concentrated sulfuric acid is added, and the whole is heated for four hours at 100° C. After cooling the pH is adjusted to 10. The product is suction filtered and 41 parts (71.9% of theory) of 4-hydrazinophenyl-3'-hydroxypropene-2'-sulfone having a melting point of 136° to 142° C. is isolated.

(c) 11.4 parts of 4-hydrazinophenyl-3'-hydroxypropene-2'-sulfone and 10.15 parts of 4-chloro-β-chloropropiophenone are boiled under reflux in 50 parts of methyl glycol for two hours. The whole is cooled and 14 parts (74.5% of theory) of the compound of the formula:

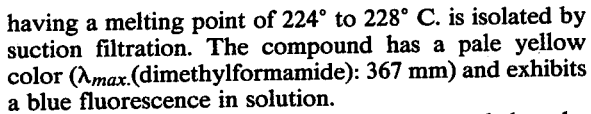

having a melting point of 224° to 228° C. is isolated by suction filtration. The compound has a pale yellow color (λ$_{max}$.(dimethylformamide): 367 mm) and exhibits a blue fluorescence in solution.

The following compounds are prepared by the method described in Example A:

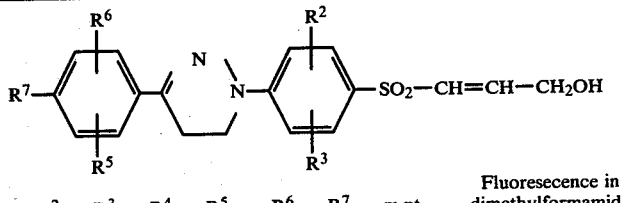

| Ex. | R$^2$ | R$^3$ | R$^4$ | R$^5$ | R$^6$ | R$^7$ | m.pt. | Fluoresecence in dimethylformamide |
|---|---|---|---|---|---|---|---|---|
| A$^1$ | H | H | H | H | 3-Cl | Cl | 222–229 | greenish blue |
| A$^2$ | H | H | H | 5-Cl | 2-CH$_3$ | Cl | 245–250 | greenish blue |
| A$^3$ | H | H | CH$_3$ | H | H | Cl | 218–226 | blue |
| A$^4$ | 2-Cl | 5-Cl | H | H | H | Cl | 256–264 | blue |

EXAMPLE B (a) 305 parts of p-acetylaminobenzenesulfinic acid is dissolved with 300 parts of sodium acetate in 1200 parts of water. 168 parts of epichlorohydrin is dripped in within two hours at 40° to 45° C. and the whole is stirred for another two hours at 40° to 45° C. The whole is allowed to cool and is suction filtered. The yield is 265 parts of 4-acetylaminophenyl-2'-hydroxy-3'-chloropropylsulfone having a melting point of 174° to 176° C. NMR (D-DMSO): 2.1(S), 3.45(D), 3.60(D), 4.1(M), 5.2(D), 7.82(S), 10.4(brS), 3:2:2:1:1:4:1—

(b) 58.4 parts of the compound from (a) is heated for one hour at 100° C. in 80 parts of water and 80 parts of concentrated hydrochloric acid. The whole is cooled and diazotized at 0° to 5° C. with a solution of 14.5 parts of sodium nitrite in 30 parts of water. Thirty minutes later the reaction mixture is poured into a solution of 150 parts of sodium sulfite in 250 parts of water and stirred for one hour at 10° to 15° C. After 70 parts of sulfuric acid has been added the whole is stirred for another hour at ambient temperature. The pH of the solution is then adjusted to 4.5 by dripping in 50% caustic soda solution; an oil thus separates and slowly crystallizes. The yield is 52 parts of 4-hydrazinophenyl-2'-hydroxy-3'-chloropropylsulfone having a melting point of 96° to 98° C. (after recrystallization from a mixture of ethyl acetate and cyclohexane).

(c) 66 parts of the compound from (b) and 51 parts of 4-chloro-β-chloropropiophenone are heated in 500 parts of ethyl alcohol for forty-five minutes at 75° to 78° C. The whole is then cooled and 75 parts of the compound of the formula:

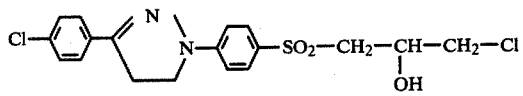

is isolated. It has a melting point of 157° to 158° C.

The following compounds are prepared by the method described in Example B:

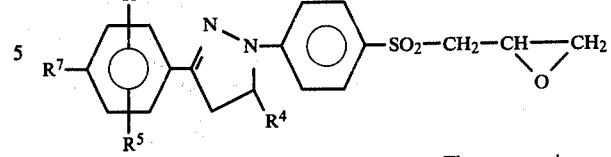

| Ex. | $R^4$ | $R^5$ | $R^6$ | $R^7$ | Fluorescence in dimethylformamide |
|---|---|---|---|---|---|
| $C_1$ | H | H | 3-Cl | Cl | greenish blue |
| $C_2$ | H | 5-Cl | 2-$CH_3$ | Cl | greenish blue |
| $C_3$ | $CH_3$ | H | 3-Cl | Cl | greenish blue |

EXAMPLE D 20.6 parts of the compound from Example B(c) and 10 parts of sodium acetate are heated in 30 parts of acetic anhydride for two hours at 100° C. The whole is allowed to cool and the product is hydrolyzed with 700 parts of water and suction filtered. 18 parts of the compound:

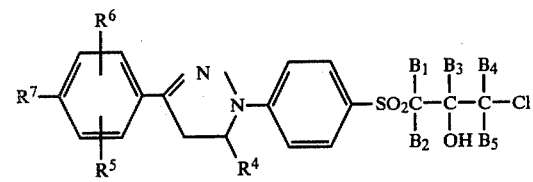

| Ex. | $R_4$ | $R_5$ | $R_6$ | $R_7$ | $B_1$ | $B_2$ | $B_3$ | $B_4$ | $B_5$ | Fluorescence dimethylformamide |
|---|---|---|---|---|---|---|---|---|---|---|
| $B_1$ | H | H | 3-Cl | Cl | H | H | H | H | H | greenish blue |
| $B_2$ | H | 5-Cl | 2-$CH_3$ | Cl | H | H | H | H | H | greenish blue |
| $B_3$ | H | H | H | Cl | $CH_3$ | H | H | H | H | blue |
| $B_4$ | H | H | H | Cl | H | H | H | $CH_3$ | H | blue |
| $B_5$ | H | H | H | Cl | H | H | $CH_3$ | H | H | blue |
| $B_6$ | H | H | H | Cl | H | H | H | $CH_3$ | $CH_3$ | blue |

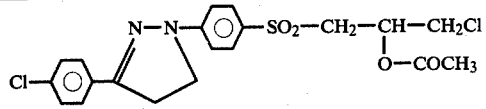

EXAMPLE C 20.6 parts of the compound from Example B(c), 5 parts of sodium acetate and 5 parts of sodium iodide are heated in 300 parts of methyl ethyl ketone for ten hours at 60° to 65° C. The whole is cooled to ambient temperature and 400 parts of water and 400 parts of petroleum ether are added. 18 parts of the compound:

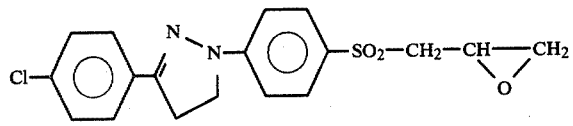

having the melting point 154° to 156° C. (after recrystallization from toluene) is isolated by suction filtration.

The natural color of the compound is pale yellow; a solution of the compound in dimethylformamide has an intensely blue fluorescence.

The following compounds are prepared by the method described in Example C:

is isolated; it has a melting point of 179° to 182° C. The compound is pale yellow in color; its solution in dimethylformamide has a greenish blue fluorescence.

EXAMPLE 1

12 parts of 1-(p-allylsulfonylphenyl)-3-(p-chlorophenyl)-$\Delta^2$-pyrazoline, 25 parts of N,N-diethylethanolamine and 0.5 part of 50% caustic soda solution are stirred for thirty minutes at 60° to 80° C.

After the whole has cooled it is stirred into water and the product is suction filtered. 14 parts of a compound of the following constitution is obtained:

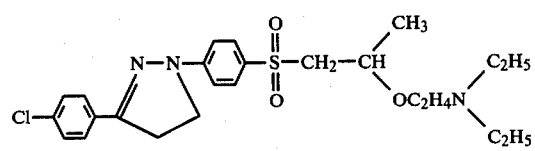

It has a melting point of 143° to 147° C.

The reaction of 22 parts of p-allylsulfonylphenylhydrazine and 22 parts of p-ω-dichloropropiophenone in 250 parts of methanol results in 28 parts of 1-(p-allylsulfonylphenyl)-3-(p-chlorophenyl)-Δ²-pyrazoline.

The compound melts at 212° to 213° C. after recrystallization from butanol. p-Allylsulfonylphenylhydrazine is obtained by the following method: 57 parts of p-allylsulfonylacetanilide is stirred with 130 parts of concentrated hydrochloric acid and 80 parts of water for two hours at refluxing temperature.

100 parts of ice is added and diazotization is carried out at 0° to 5° C. with 18 parts of sodium nitrite dissolved in 40 parts of water. The diazonium salt solution is allowed to flow at 0° to 8° C. into a solution of 100 parts of sodium sulfite and 400 parts of water and stirring is continued for another hour. The solution is made acid with 170 parts of sulfuric acid and stirred for another four hours at 90° to 95° C. After the whole has been cooled and the pH adjusted to 8 to 9 40 parts of p-allylsulfonylphenylhydrazine is precipitated. After the hydrazine has been recrystallized from toluene it has a melting point of 90° to 91° C.

p-Allylsulfonylacetanilide may be prepared as follows:

50 parts of p-acetylaminophenylsulfinic acid and 25 parts of sodium hydrogen carbonate are suspended in 300 parts of water. While stirring intensely 36 parts of allyl bromide is dripped in within three hours at 50° to 60° C. Stirring is continued for another four hours at 60° C. 45 parts of p-allylsulfonylacetanilide is obtained with a melting point of 116° to 118° C.

EXAMPLE 2

13 parts of 1-(p-allylsulfonylphenyl)-3-(p-chlorophenyl)-Δ²-pyrazoline, 25 parts of morpholine and 0.5 part of 50% caustic soda solution are stirred for three hours at 80° to 90° C. After the whole has been cooled it is stirred into 200 parts of ice. 15.5 parts of the following compound is obtained:

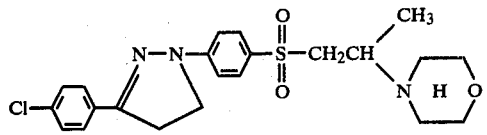

It has a melting point of 155° to 162° C.

EXAMPLE 3

12 parts of 1-(p-allylsulfonylphenyl)-3-(p-chlorophenyl)-Δ²-pyrazoline and 25 parts of N-methylpiperazine are stirred for one hour at 100° C. When cold the whole is poured onto ice. 13 parts of the compound of the following constitution:

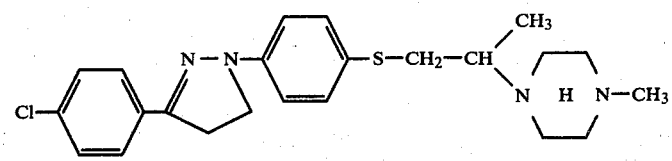

is obtained. After having been stirred with petroleum ether the amorphous compound melts at 45° to 55° C.

EXAMPLE 4

10 parts of 1-(p-allylsulfonylphenyl)-3-(p-chlorophenyl)-Δ²-pyrazoline and 25 parts of N-2-aminobutyl-piperidine are stirred for six hours at 100° C. After the whole has been cooled it is stirred into 200 parts of ice. The oily residue is dried and then stirred with petroleum ether. 12 parts of an amorphous compound is obtained having a melting point of 70° to 82° C. and the following structure:

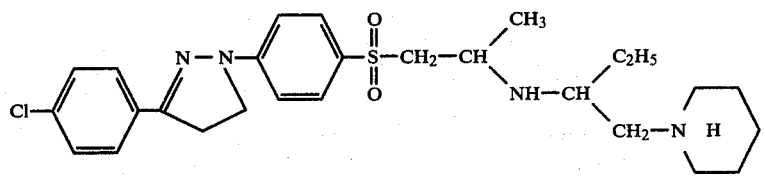

EXAMPLE 5

10 parts of 1-(p-allylsulfonylphenyl)-3-(p-chlorophenyl)-Δ²-pyrazoline and 25 parts of butylamine are stirred for five hours at 80° C. After the whole has been cooled it is stirred into 150 parts of ice. 12 parts of the following compound is obtained:

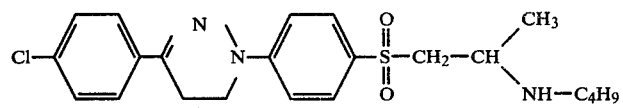

It has a melting point of 112° to 114° C.

EXAMPLE 6

The following compound:

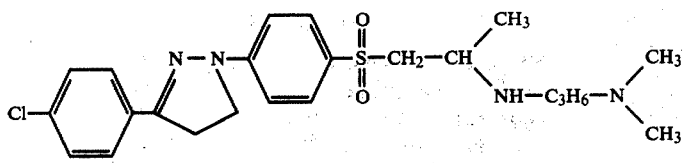

is obtained analogously to Example 5 with dimethylaminopropylamine. After the compound has been recrystallized from methylcyclohexane it melts at 102° to 103° C.

EXAMPLE 7

12 parts of 1-(p-allylsulfonylphenyl)-3-(p-chlorophenyl)-Δ²-pyrazoline, 25 parts of N,N-dimethylpropanolamine and 1 part of 30% caustic potash solution are stirred for fifteen minutes at 70° to 80° C. After the whole has cooled it is stirred into water and suction filtered. 14 parts of the following compound is obtained:

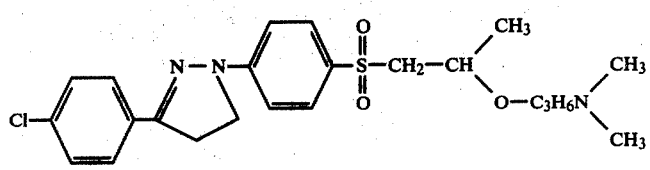

It has a melting point of 138° to 139° C.

EXAMPLE 8

The reaction according to Example 7 is carried out in N,N-dimethylethanolamine. The following compound is obtained in a quantitative yield:

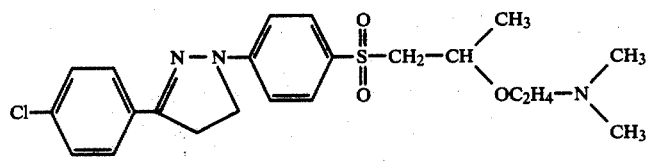

It has a melting point of from 150° to 151° C.

EXAMPLE 9

12 parts of 1-(p-allylsulfonylphenyl)-3-(p-chlorophenyl)-Δ²-pyrazoline, 30 parts of N-methylpyrrolidone, 10 parts of water and 1 part of 50% caustic soda solution are stirred for sixty minutes at 80° to 90° C. The whole is cooled and made acid and then stirred into ice. 12 parts of a compound of the following constitution is obtained.

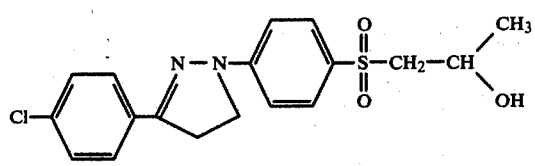

It has a melting point of 160° to 162° C.

EXAMPLE 10

10 parts of the compound from Example 9 is stirred at ambient temperature into 60 parts of concentrated sulfuric acid. The whole is stirred for another twenty hours and poured onto ice. The precipitated product of the following constitution is isolated:

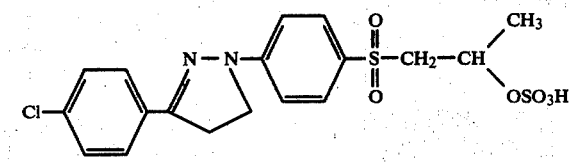

EXAMPLE 11

5 parts of 1-p-(methallylsulfonylphenyl)-3-(p-chlorophenyl)-Δ²-pyrazoline and 30 parts of ethanolamine are stirred for four hours at 120° C. After cooling the product is precipitated with water and suction filtered. 5 parts of the following compound is obtained:

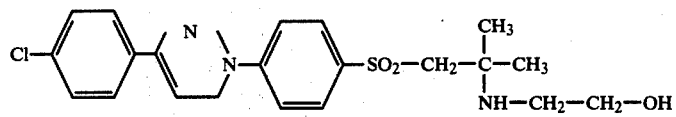

It has a melting point of 178° to 179° C.

1-p-(methallylsulfonylphenyl)-3-(p-chlorophenyl)-Δ²-pyrazoline is obtained by the reaction of p-methallylsulfonylphenylhydrazine with 4,ω-dichloropropiophenone in methanol. It has a melting point of 180° to 182° C.

p-Methallylsulfonylphenylhydrazine is obtained as follows: p-methallylsulfonylacetanilide is converted into the aniline derivative. Diazotization and reduction with sodium sulfite gives p-methallylsulfonylphenylhydrazine in a yield of 80 to 85% of theory. The melting point is 95° to 98° C.

a yield of 75 to 80% of theory. The melting point is 115° to 116° C.

EXAMPLE 14

10 parts of 1-(p-crotylsulfonylphenyl)-3-(p-chlorophenyl)-$\Delta^2$-pyrazoline, 20 parts of N,N-dimethylpropanolamine and 1 part of saturated sodium carbonate solution are stirred for sixty minutes at 90° C. 11 parts of the following compound is obtained:

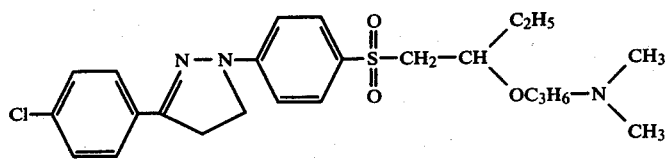

EXAMPLE 12

5 parts of 1-p-(allylsulfonylphenyl)-3-(p-chlorophenyl)-$\Delta^2$-pyrazoline and 30 parts of diethanolamine are stirred for three hours at 120° C. After the whole has been cooled the product is precipitated with water and suction filtered. 5.3 parts of the following compound is obtained:

EXAMPLE 15

10 parts of 1-(p-allylsulfonylphenyl)-3-(p-chlorophenyl)-$\Delta^2$-pyrazoline, 20 parts of 2-ethylhexyl alcohol and 1 part of 50% caustic soda solution are stirred at 80° C. for thirty minutes. The following compound is obtained in a quantitative yield:

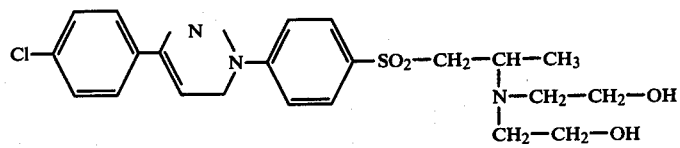

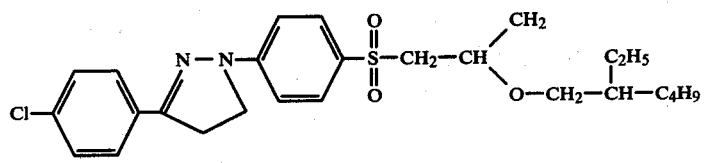

It has a melting point of 72° to 74° C.

It has a melting point of 152° to 155° C.

EXAMPLE 13

10 parts of 1-(p-crotylsulfonylphenyl)-3-(p-chlorophenyl)-$\Delta^2$-pyrazoline, 20 parts of diethylethanolamine and 1 part of 30% caustic soda solution are stirred for forty-five minutes at 70° to 80° C.

After the whole has been cooled it is stirred into water and suction filtered. 11 parts of a compound of the following constitution is obtained:

EXAMPLE 16

10 parts of 1-(p-allylsulfonylphenyl)-$\Delta^2$-pyrazoline, 20 parts of ethyl glycol and 1 part of 50% caustic soda solution are stirred for forty-five minutes at 80° C. 12 parts of the following compound is obtained:

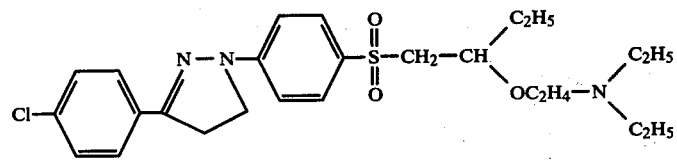

1-(p-crotylsulfonylphenyl)-3-(p-chlorophenyl)-$\Delta^2$-pyrazoline is obtained by the reaction of p-crotylsulfonylphenylhydrazine with p-$\omega$-dichloropropiophenone in methanol. The compound melts at 123° to 124° C. after it has been recrystallized from isobutanol.

p-Crotylsulfonylphenylhydrazine is obtained as follows: p-crotylsulfonylacetanilide is converted into the aniline derivative. Diazotization and reduction with sodium sulfite gives p-crotylsulfonylphenylhydrazine in

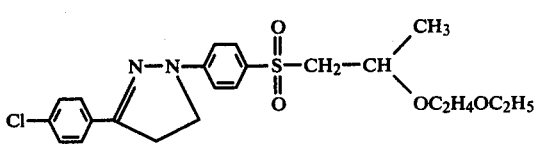

It has a melting point of 102° to 104° C.

EXAMPLE 17

The reaction described in Example 16 is carried out with methyl diglycol. 13 parts of the following compound is obtained:

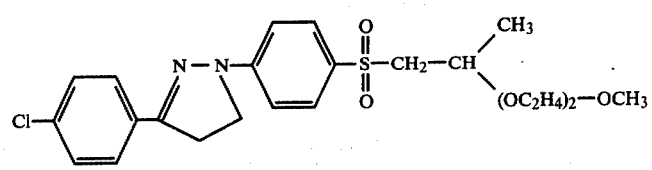

It has a melting point of 176° to 177° C.

EXAMPLE 18

10.8 parts of 1-(p-allylsulfonyl)-3-(p-chlorophenyl)-Δ²-pyrazoline, 20 parts of N-methylpyrrolidone, 30 parts of water, 7.5 parts of taurine and 5.3 parts of 50% caustic soda solution are stirred for about thirty minutes at 90° C. until a sample has good solubility in water. 11 parts of the following compound crystallizes out in the neutral region:

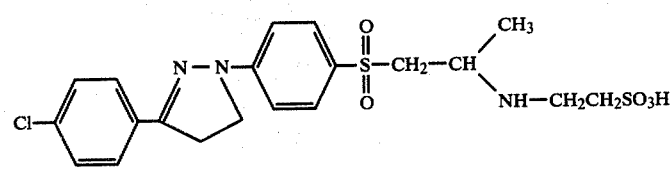

It has a melting point of 245° to 248° C.

EXAMPLE 19

10 parts of 1-(p-allylsulfonylphenyl)-3-(p-chlorophenyl)-Δ²-pyrazoline, 6 parts of acetamide and 0.5 part of sodium methylate are heated to 100° C. Twenty minutes later the melt is allowed to cool and crystallized from glacial acetic acid. 8 parts of the following compound is obtained:

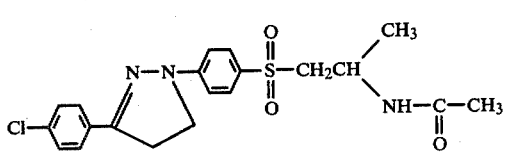

It has a melting point of 198° to 199° C.

EXAMPLE 20

10 parts of the compound from Example 7 is dissolved in 30 parts of toluene. While stirring 4 parts of dimethyl sulfate is dripped in at 80° C. 12 parts of product of the following constitution is isolated as an oil:

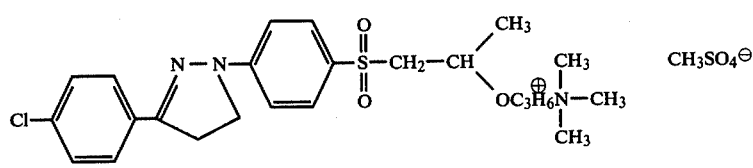

EXAMPLE 21

12 parts of 1-(p-allylsulfonylphenyl)-3-(p-chlorophenyl)-Δ²-pyrazoline, 25 parts of N-hydroxyethylmorpholine and 1 part of 30% caustic soda solution are stirred for twenty-five minutes at 70° to 80° C. The product is stirred into water. 14 parts of the following compound is obtained:

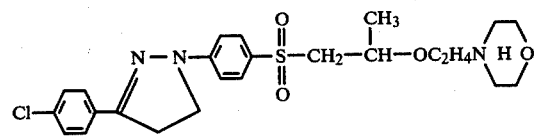

It has a melting point of 144° to 145° C.

EXAMPLE 22

10 parts of the compound from Example 21 is dissolved in 30 parts of toluene. While stirring 4 parts of methyl iodide is dripped in at 100° C. and the whole is stirred for another four hours. 12 parts of the following compound is isolated as an amorphous product:

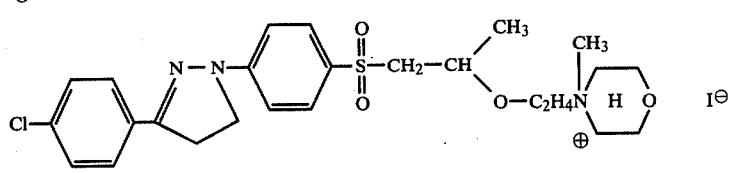

EXAMPLE 23

10 parts of 1-(p-allylsulfonylphenyl)-3-(p-chlorophenyl)-Δ²-pyrazoline and 25 parts of 2-ethylhexylamine are stirred for five hours at refluxing temperature.

The product is stirred into water. 12 parts of the following compound is obtained:

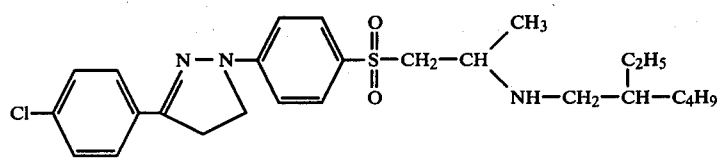

It has a melting point of 74° to 75° C.

EXAMPLE 24

The 2-ethylhexylamine used in Example 23 is replaced by piperidine. The following compound is obtained in a quantitative yield:

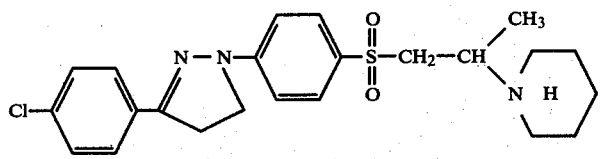

It has a melting point of 164° to 165° C.

EXAMPLE 25

The 2-ethylhexylamine is Example 23 is replaced by hexamethyleneimine. A quantitative yield of the following compound is obtained:

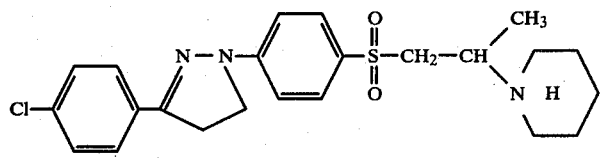

It has a melting point of 79° to 80° C.

The following compounds may be prepared according to the Examples given:

Table I

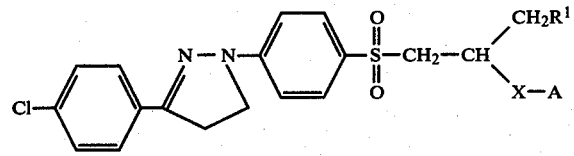

| Ex. | $R^1$ | X—A | Dissolved in | Shade of fluorescence |
|---|---|---|---|---|
| 26 | H | $OCH_3$ | dimethylformamide | violet |
| 27 | H | $OC_2H_5$ | " | " |
| 28 | H | $OC_3H_7$ | " | " |
| 29 | H | $OC_6H_{13}$ | " | " |
| 30 | H | $OC_8H_{17}$ | " | " |
| 31 | H | $OC_{10}H_{21}$ | " | " |
| 32 | H | $OC_2H_4OH$ | " | " |
| 33 | H | $OCH_2-CH-OH$ <br> $\quad\quad\quad\;\; |$ <br> $\quad\quad\quad CH_3$ | | |
| 34 | H | $OC_6H_{12}OH$ | " | " |
| 35 | H | $OC_2H_4OC_2H_4OH$ | " | " |
| 36 | H | $OC_2H_4OCH_3$ | " | " |
| 37 | H | $OC_2H_4OC_4H_9$ | " | " |
| 38 | H | $OC_3H_6OC_8H_{17}$ | " | " |
| 39 | H | $OC_2H_4(OC_2H_4)_2OCH_3$ | " | " |
| 40 | H | $OC_2H_4SCH_3$ | " | " |
| 41 | H | $OC_2H_4SC_6H_5$ | " | " |
| 42 | H | $OC_2H_4CN$ | " | " |
| 43 | H | $OC_2H_4OC_2H_4CN$ | " | " |
| 44 | H | $OC_2H_4Cl$ | " | " |
| 45 | H | $OC_4H_8Cl$ | " | " |
| 46 | H | $OC_6H_{12}Cl$ | " | " |
| 47 | H | $OC_3H_6Br$ | " | " |
| 48 | H | $OC_2H_4COOH$ | dilute alkali | bluish violet |
| 49 | H | $OC_2H_4COOCH_3$ | dimethylformamide | violet |
| 50 | H | $OC_2H_4N(C_3H_7)_2$ | dilute acid | bluish violet |
| 51 | H | $OC_2H_4N(C_4H_9)_2$ | " | " |

Table I-continued

Structure: 4-chlorophenyl-pyrazoline-N-phenyl-SO$_2$-CH$_2$-CH(CH$_2$R$^1$)(X-A)

| Ex. | R$^1$ | X—A | Dissolved in | Shade of fluorescence |
|---|---|---|---|---|
| 52 | H | OC$_2$H$_4$N(CH$_3$)(C$_4$H$_9$) | " | " |
| 53 | H | OC$_2$H$_4$N(CH$_3$)(C$_6$H$_{11}$) | " | " |
| 54 | H | OC$_2$H$_4$N(CH$_3$)(C$_8$H$_{17}$) | " | " |
| 55 | H | OC$_3$H$_6$N(C$_2$H$_5$)$_2$ | " | " |
| 56 | H | OC$_3$H$_6$N(C$_3$H$_7$)$_2$ | " | " |
| 57 | H | OC$_3$H$_6$N(C$_4$H$_9$)$_2$ | " | " |
| 58 | H | OC$_3$H$_6$N(CH$_3$)(C$_2$H$_5$) | | |
| 59 | H | OC$_3$H$_6$N(C$_2$H$_5$)(C$_4$H$_9$) | " | " |
| 60 | H | OC$_4$H$_8$—N(CH$_3$)$_2$ | " | " |
| 61 | H | OC$_4$H$_8$—N(C$_2$H$_5$)$_2$ | " | " |
| 62 | H | OC$_4$H$_8$—N(C$_3$H$_7$)$_2$ | " | " |
| 63 | H | OC$_4$H$_8$—N(CH$_3$)(C$_4$H$_9$) | | |
| 64 | H | OC$_4$H$_8$—N(CH$_3$)(C$_6$H$_{11}$) | " | " |
| 65 | H | OC$_6$H$_{12}$—N(CH$_3$)$_2$ | " | " |
| 66 | H | OC$_6$H$_{12}$—N(C$_2$H$_5$)$_2$ | " | " |
| 67 | H | OC$_6$H$_{12}$N(C$_4$H$_9$)$_2$ | " | " |
| 68 | H | OC$_6$H$_{12}$N(CH$_3$)(C$_2$H$_5$) | | |
| 69 | H | OC$_6$H$_{12}$N(C$_2$H$_5$)(C$_4$H$_9$) | " | " |
| 70 | H | OC$_6$H$_{12}$N(C$_3$H$_5$)(C$_5$H$_{11}$) | " | " |
| 71 | H | OCH$_2$—CH(CH$_3$)—N(CH$_3$)$_2$ | " | " |
| 72 | H | OCH$_2$—CH(CH$_3$)—N(C$_2$H$_5$)$_2$ | " | " |
| 73 | H | OCH$_2$—CH(CH$_3$)—N(C$_4$H$_9$)$_2$ | " | " |

Table I-continued

Structure: 4-chlorophenyl-pyrazoline-N-phenyl-SO₂-CH₂-CH(CH₂R¹)(X-A)

| Ex. | R¹ | X—A | Dissolved in | Shade of fluorescence |
|---|---|---|---|---|
| 74 | H | OCH₂—CH(CH₃)—N(CH₃)(C₂H₅) | " | " |
| 75 | H | OC₂H₄—N(pyrrolidine)H | " | " |
| 76 | H | OC₃H₆—N(pyrrolidine)H | " | " |
| 77 | H | OC₄H₈—N(pyrrolidine)H | " | " |
| 78 | H | OCH₂—CH(CH₃)—N(piperidine)H | " | " |
| 79 | H | OC₂H₄—N(piperidine)H | " | " |
| 80 | H | OC₃H₆—N(piperidine)H | " | " |
| 81 | H | OC₄H₈—N(piperidine)H | " | " |
| 82 | H | OC₆H₁₂—N(piperidine)H | " | " |
| 83 | H | OCH₂—CH(CH₃)—N(piperidine)H | " | " |
| 84 | H | OC₂H₄—N(hexamethyleneimine)H | " | " |
| 85 | H | OC₃H₆—N(hexamethyleneimine)H | " | " |
| 86 | H | OC₄H₈—N(hexamethyleneimine)H | " | " |

Table I-continued

Structure: 4-chlorophenyl-pyrazoline-N-phenyl-SO$_2$-CH$_2$-CH(CH$_2$R$^1$)(X-A)

| Ex. | R$^1$ | X—A | Dissolved in | Shade of fluorescence |
|---|---|---|---|---|
| 87 | H | OC$_6$H$_{12}$N(hexamethyleneimine) | " | " |
| 88 | H | OC$_3$H$_6$—N(morpholine) | " | " |
| 89 | H | OC$_4$H$_8$—N(morpholine) | " | " |
| 90 | H | OC$_6$H$_{12}$—N(morpholine) | " | " |
| 91 | H | OCH$_2$—CH(CH$_3$)—N(morpholine) | " | " |
| 92 | H | OC$_2$H$_4$—N(N'-methylpiperazine) | " | " |
| 93 | H | OC$_3$H$_6$—N(N'-methylpiperazine) | " | " |
| 94 | H | OC$_4$H$_8$—N(N'-methylpiperazine) | " | " |
| 95 | H | OC$_2$H$_4$—N(N'-hydroxyethylpiperazine) | " | " |
| 96 | H | OC$_3$H$_6$—N(N'-hydroxyethylpiperazine) | " | " |
| 97 | H | OC$_2$H$_4$—N—N (pyrazole) | dimethylformamide | violet |
| 98 | H | OCH$_2$—CH(CH$_3$)—N—N (pyrazole) | " | " |
| 99 | H | OC$_2$H$_4$—N—N (3,5-dimethylpyrazole) | " | " |
| 100 | H | OC$_2$H$_4$—N—N (3-methyl-5-phenylpyrazole) | " | " |
| 101 | H | OC$_2$H$_4$—N—N (5-methylpyrazole) | " | " |
| 102 | H | OC$_2$H$_4$N$^{\oplus}$(CH$_3$)$_3$ CH$_3$SO$_4^{\ominus}$ | water | bluish violet |
| 103 | H | OC$_2$H$_4$N$^{\oplus}$(C$_2$H$_5$)$_2$(CH$_3$) CH$_3$SO$_4^{\ominus}$ | " | " |

Table I-continued

[Structure: 3-(4-chlorophenyl)-1-(4-sulfonylphenyl)-4,5-dihydropyrazole with -SO₂-CH₂-CH(CH₂R¹)(X-A) substituent]

| Ex. | R¹ | X—A | Dissolved in | Shade of fluorescence |
|---|---|---|---|---|
| 104 | H | OC₂H₄—N⁺(CH₃)₂(C₂H₅) C₂H₅SO₄⁻ | " | " |
| 105 | H | OC₂H₄—N⁺(C₄H₉)(CH₃)₂ Br⁻ | " | " |
| 106 | H | OC₃H₆—N⁺(CH₃)₃ CH₃SO₄⁻ | " | " |
| 107 | H | OC₃H₆—N⁺(CH₃)(C₂H₅)₂ I⁻ | " | " |
| 108 | H | OC₃H₆—N⁺(C₄H₉)(CH₃)₂ CH₃SO₄⁻ | " | " |
| 109 | H | OC₃H₆—N⁺(C₆H₁₃)(CH₃)₂ CH₃SO₄⁻ | " | " |
| 110 | H | OC₄H₈N⁺(CH₃)₃ CH₃SO₄⁻ | " | " |
| 111 | H | OC₄H₈—N⁺(CH₃)(C₂H₅)₂ BF₄⁻ | " | " |
| 112 | H | OC₆H₁₂N⁺(CH₃)₃ CH₃SO₄⁻ | " | " |
| 113 | H | OC₆H₁₂N⁺(C₂H₅)(CH₃)₂ CH₃SO₄⁻ | " | " |
| 114 | H | OCH₂—CH(CH₃)—N⁺(CH₃)₃ CH₃SO₄⁻ | " | " |
| 115 | H | OC₂H₄—N⁺(CH₃)(piperidine) CH₃SO₄⁻ | " | " |
| 116 | H | OC₃H₆—N⁺(CH₃)(piperidine) CH₃SO₄⁻ | " | " |
| 117 | H | OC₄H₈—N⁺(C₂H₅)(piperidine) Br⁻ | " | " |
| 118 | H | OCH₂—CH(CH₃)—N⁺(CH₃)(piperidine) CH₃SO₄⁻ | " | " |
| 119 | H | OC₂H₄—N⁺(CH₃)(piperidine) CH₃SO₄⁻ | " | " |
| 120 | H | OC₃H₆—N⁺(CH₃)(piperidine) BF₄⁻ | " | " |

Table I-continued

Structure: 4-chlorophenyl-pyrazoline-N-phenyl-SO$_2$-CH$_2$-CH(CH$_2$R$^1$)(X-A)

| Ex. | R$^1$ | X—A | Dissolved in | Shade of fluorescence |
|---|---|---|---|---|
| 121 | H | OCH$_2$-CH(CH$_3$)-N$^\oplus$(CH$_3$)(H)-piperidine  I$^\ominus$ | " | " |
| 122 | H | OC$_2$H$_4$-N$^\oplus$(CH$_3$)(H)-hexahydroazepine  BF$_4^\ominus$ | " | " |
| 123 | H | OC$_3$H$_6$-N$^\oplus$(C$_2$H$_5$)(H)-hexahydroazepine  CH$_3$COO$^\ominus$ | " | " |
| 124 | H | OC$_3$H$_6$-N$^\oplus$(CH$_3$)(H)-hexahydroazepine  ClO$_4^\ominus$ | " | " |
| 125 | H | OC$_2$H$_4$-N$^\oplus$(CH$_3$)(H)-morpholine  F$_3$C—COO$^\ominus$ | " | " |
| 126 | H | OC$_3$H$_6$-N$^\oplus$(C$_2$H$_5$)(H)-morpholine  C$_6$H$_5$SO$_3^\ominus$ | " | " |
| 127 | H | OCH$_2$-CH(CH$_3$)-N$^\oplus$(CH$_3$)(H)-morpholine  CH$_3$SO$_4^\ominus$ | " | " |
| 128 | H | OC$_2$H$_4$-N-piperazine-N$^\oplus$(CH$_3$)$_2$(H)  Br$^\ominus$ | " | " |
| 129 | H | OC$_2$H$_4$-N-piperazine-N$^\oplus$(CH$_3$)(C$_2$H$_5$)(H)  Cl$^\ominus$ | " | " |
| 130 | H | OC$_3$H$_6$-N-piperazine-N$^\oplus$(CH$_3$)$_2$(H)  CH$_3$SO$_4^\ominus$ | " | " |
| 131 | H | OC$_2$H$_4$-N$^\oplus$=N—CH$_3$ (imidazolium)  CH$_3$SO$_4^\ominus$ | " | " |
| 132 | H | OC$_2$H$_4$-N$^\oplus$=N—CH$_3$ (pyrazolium)  CH$_3$SO$_4^\ominus$ | " | " |

Table I-continued

Structure: 4-chlorophenyl-pyrazoline-N-phenyl-SO$_2$-CH$_2$-CH(X-A)-CH$_2$R$^1$

| Ex. | R$^1$ | X—A | Dissolved in | Shade of fluorescence |
|---|---|---|---|---|
| 133 | H | O—C$_6$H$_{11}$ (cyclohexyl) | dimethylformamide | violet |
| 134 | H | O—C$_5$H$_9$ (cyclopentyl) | " | " |
| 135 | H | OCH$_2$—C$_6$H$_5$ | | |
| 136 | H | OCH$_2$—C$_6$H$_4$SO$_3$H | dilute alkali | bluish violet |
| 137 | H | OC$_2$H$_4$C$_6$H$_4$SO$_3$H | " | " |
| 138 | H | OC$_6$H$_4$SO$_3$H | " | " |
| 139 | H | OC$_6$H$_3$(SO$_3$H)$_2$ | " | " |
| 140 | H | OC$_2$H$_4$C$_6$H$_5$ | dimethylformamide | violet |
| 141 | H | OC$_6$H$_4$CH$_3$ | " | " |
| 142 | H | OC$_2$H$_4$—C$_6$H$_4$CH$_3$ | " | " |
| 143 | H | OC$_6$H$_5$ | " | " |
| 144 | H | OC$_6$H$_5$OC$_2$H$_5$ | " | " |
| 145 | H | NH—CH$_3$ | " | " |
| 146 | H | NHC$_2$H$_5$ | " | " |
| 147 | H | NHC$_3$H$_7$ | " | " |
| 148 | H | NHC$_5$H$_{11}$ | " | " |
| 149 | H | NHC$_6$H$_{13}$ | " | bluish violet |
| 150 | H | NHC$_7$H$_{15}$ | " | " |
| 151 | H | NHC$_8$H$_{17}$ | " | " |
| 152 | H | NHC$_9$H$_{19}$ | " | " |
| 153 | H | NHC$_{10}$H$_{21}$ | " | " |
| 154 | H | NHC$_{13}$H$_{27}$ | " | " |
| 155 | H | NHC$_2$H$_4$OH | " | " |
| 156 | H | NHC$_3$H$_6$OH | " | " |
| 157 | H | NHC$_6$H$_{12}$OH | " | " |
| 158 | H | NHC$_2$H$_4$OCH$_3$ | " | " |
| 159 | H | NHC$_3$H$_6$OCH$_3$ | " | " |
| 160 | H | NHC$_2$H$_4$OC$_2$H$_5$ | " | " |
| 161 | H | NHC$_3$H$_6$OC$_2$H$_5$ | " | " |
| 162 | H | NHC$_2$H$_4$OC$_8$H$_{17}$ | " | " |
| 163 | H | NHC$_3$H$_6$OC$_8$H$_{17}$ | " | " |
| 164 | H | NHC$_2$H$_4$OC$_2$H$_4$OC$_6$H$_5$ | " | " |
| 165 | H | NH—C$_2$H$_4$OC$_2$H$_4$OCH$_3$ | " | " |
| 166 | H | NH—C$_2$H$_4$CN | " | " |
| 167 | H | NH—C$_5$H$_{10}$CN | " | " |
| 168 | H | NH—C$_6$H$_{12}$CN | " | " |
| 169 | H | NH—C$_2$H$_4$COOH | dilute alkali | blue |
| 170 | H | NHC$_2$H$_4$COOCH$_3$ | dimethylformamide | bluish violet |
| 171 | H | NHC$_2$H$_4$COOC$_4$H$_9$ | " | " |
| 172 | H | NH—C$_2$H$_4$CONH$_2$ | " | " |
| 173 | H | NHC$_2$H$_4$CONHC$_2$H$_5$ | " | " |
| 174 | H | NHC$_2$H$_4$CONHC$_6$H$_{13}$ | " | " |
| 175 | H | NH—C$_2$H$_4$—N(pyrrolidinone) | " | " |
| 176 | H | NH—C$_3$H$_6$—N(pyrrolidinone) | " | " |
| 177 | H | NH—C$_2$H$_4$—NHC$_2$H$_5$ | dilute acid | blue |
| 178 | H | NHC$_2$H$_4$—NHC$_3$H$_7$ | " | " |
| 179 | H | NHC$_2$H$_4$—NH—C$_6$H$_{11}$ (cyclohexyl) | | |

Table I-continued

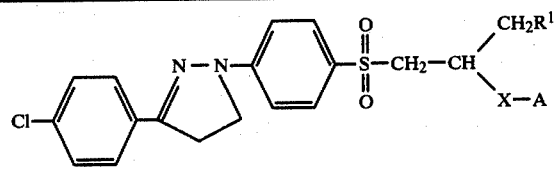

| Ex. | R¹ | X—A | Dissolved in | Shade of fluorescence |
|---|---|---|---|---|
| 180 | H | NHC₂H₄N(CH₃)(CH₃) | " | " |
| 181 | H | NHC₂H₄N(C₂H₅)(C₂H₅) | " | " |
| 182 | H | NHC₂H₄—N(C₃H₇)(C₃H₇) | " | " |
| 183 | H | NH—C₂H₄N(C₄H₉)(C₄H₉) | " | " |
| 184 | H | NH—C₂H₄N(CH₃)(C₄H₉) | " | " |
| 185 | H | NHC₃H₆N(C₂H₅)(C₂H₅) | " | " |
| 186 | H | NHC₃H₆N(C₄H₉)(C₄H₉) | " | " |
| 187 | H | NH—C₃H₆—N(CH₃)(C₂H₅) | " | " |
| 188 | H | NHC₃H₆—N(CH₃)(C₆H₁₁) | " | " |
| 189 | H | NHC₃H₆—N(CH₃)(C₆H₁₃) | " | " |
| 190 | H | NHC₃H₆—N(C₂H₅)(C₄H₉) | " | " |
| 191 | H | NH—C₄H₈—N(CH₃)(CH₃) | " | " |
| 192 | H | NH—C₄H₈—N(C₂H₅)(C₂H₅) | " | " |
| 193 | H | NH—C₆H₁₂—N(CH₃)(CH₃) | " | " |
| 194 | H | NH—C₆H₁₂—N(CH₃)(C₄H₉) | " | " |

Table I-continued

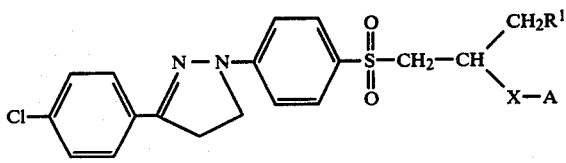

| Ex. | R[1] | X—A | Dissolved in | Shade of fluorescence |
|---|---|---|---|---|
| 195 | H | NH—CH(CH₃)—CH₂—N(CH₃)₂ | " | " |
| 196 | H | NH—CH(CH₃)—CH₂—N(C₂H₅)₂ | " | " |
| 197 | H | NH—CH(CH₃)—CH₂—N(C₄H₉)₂ | " | " |
| 198 | H | NH—CH₂—CH(CH₃)—N(CH₃)₂ | " | " |
| 199 | H | NH—CH₂—CH(CH₃)—N(C₂H₅)₂ | " | " |
| 200 | H | NHCH₂—CH(CH₃)—N(C₄H₉)₂ | " | " |
| 201 | H | NH—CH(C₂H₅)—CH₂—N(CH₃)₂ | " | " |
| 202 | H | NH—CH(C₂H₅)—CH₂—N(C₂H₅)₂ | " | " |
| 203 | H | NH—CH(C₂H₅)—CH₂—N(C₄H₉)₂ | " | " |
| 204 | H | NH—CH₂—C(CH₃)₂—CH₂N(CH₃)₂ | " | " |
| 205 | H | NH—CH₂—C(CH₃)₂—CH₂N(C₂H₅)₂ | " | " |
| 206 | H | NH—CH(C₃H₇)—CH₂—N(C₂H₅)₂ | " | " |
| 207 | H | NH—C₂H₄N⟨pyrrolidine⟩ | " | " |
| 208 | H | NH—C₃H₆N⟨pyrrolidine⟩ | " | " |
| 209 | H | NH—CH(CH₃)—CH₂—N⟨pyrrolidine⟩ | " | " |

Table I-continued

Structure: 4-Cl-C$_6$H$_4$-pyrazoline-N-C$_6$H$_4$-SO$_2$-CH$_2$-CH(X—A)-CH$_2$R$^1$

| Ex. | R$^1$ | X—A | Dissolved in | Shade of fluorescence |
|-----|-------|-----|--------------|------------------------|
| 210 | H | NH—CH(C$_2$H$_5$)—CH$_2$—N(pyrrolidine) | " | " |
| 211 | H | NH—C$_2$H$_4$—N(piperidine) | " | " |
| 212 | H | NH—C$_3$H$_6$—N(piperidine) | " | " |
| 213 | H | NH—CH(CH$_3$)—CH$_2$—N(piperidine) | " | " |
| 214 | H | NH—CH(C$_2$H$_5$)—CH$_2$—N(piperidine) | " | " |
| 215 | H | NH—C$_2$H$_4$—N(hexamethyleneimine) | " | " |
| 216 | H | NHC$_3$H$_6$—N(hexamethyleneimine) | " | " |
| 217 | H | NH—CH(CH$_3$)—CH$_2$—N(hexamethyleneimine) | " | " |
| 218 | H | NH—CH(C$_2$H$_5$)—CH$_2$—N(hexamethyleneimine) | " | " |
| 219 | H | NH—C$_2$H$_4$—N(morpholine) | " | " |
| 220 | H | NH—C$_3$H$_6$N(morpholine) | " | " |
| 221 | H | NH—CH(CH$_3$)—CH$_2$—N(morpholine) | " | " |
| 222 | H | NH—CH(C$_2$H$_5$)—CH$_2$—N(morpholine) | " | " |
| 223 | H | NH—C$_2$H$_4$—N(N'-methylpiperazine) | " | " |

Table I-continued

Structure:

4-chlorophenyl—C(=N-N<)—CH₂— (pyrazoline ring) —N—C₆H₄—SO₂—CH₂—CH(CH₂R¹)—X—A

| Ex. | R¹ | X—A | Dissolved in | Shade of fluorescence |
|---|---|---|---|---|
| 224 | H | NH—C₃H₆—N(piperazine-H)N—CH₃ | " | " |
| 225 | H | NH—CH(CH₃)—CH₂—N(piperazine-H)N—CH₃ | " | " |
| 226 | H | NH—CH(C₂H₅)—CH₂—N(piperazine-H)N—CH₃ | " | " |
| 227 | H | NH—C₂H₄—N⁺(CH₃)₃ CH₃SO₄⁻ | water | " |
| 228 | H | NH—C₂H₄—N⁺(CH₃)(C₂H₅)₂ I⁻ | " | " |
| 229 | H | NH—C₃H₆N⁺(CH₃)₃ CH₃SO₄⁻ | " | " |
| 230 | H | NH—C₃H₆N⁺(CH₃)(C₂H₅)₂ Cl⁻ | " | " |
| 231 | H | NH—C₃H₆N⁺(CH₃)(C₄H₉)₂ CH₃SO₄⁻ | " | " |
| 232 | H | NH—CH(CH₃)—CH₂—N⁺(CH₃)(C₄H₉)₂ CH₃SO₄⁻ | " | " |
| 233 | H | NH—CH(C₂H₅)—CH₂—N⁺(CH₃)(C₄H₉)₂ BF₄⁻ | " | " |
| 234 | H | NH—C₂H₄—N⁺(pyrrolidine-H)(CH₃) CH₃SO₄⁻ | " | " |
| 235 | H | NH—C₃H₆—N⁺(pyrrolidine-H)(CH₃) C₆H₅SO₃⁻ | " | " |
| 236 | H | NH—C₃H₆—N⁺(piperidine-H)(CH₃) CH₃SO₄⁻ | " | " |
| 237 | H | NH—CH(CH₃)—CH₂—N⁺(piperidine-H)(CH₃) Br⁻ | " | " |
| 238 | H | NH—CH(C₂H₅)—CH₂—N⁺(piperidine-H)(CH₃) CH₃SO₄⁻ | " | " |

Table I-continued

[Structure: 4-chlorophenyl-pyrazoline-phenyl-SO2-CH2-CH(CH2R¹)-X-A]

| Ex. | R¹ | X—A | Dissolved in | Shade of fluorescence |
|---|---|---|---|---|
| 239 | H | NH—C₂H₄—N⁺(H)(CH₃)(piperidine) CH₃SO₄⁻ | " | " |
| 240 | H | NH—C₃H₆—N⁺(H)(CH₃)(hexamethyleneimine) CH₃SO₄⁻ | " | " |
| 241 | H | NH—CH(CH₃)—CH₂—N⁺(H)(CH₃)(hexamethyleneimine) CH₃SO₄⁻ | " | " |
| 242 | H | N-pyrrolidinyl (N H) | dimethylformamide | bluish violet |
| 243 | C₂H₅ | N-piperidinyl (N H) | " | " |
| 244 | C₂H₅ | N-(4-methylpiperazinyl) | " | " |
| 245 | H | N-(4-ethylpiperazinyl) | " | " |
| 246 | H | —N—N (pyrazol-1-yl) | " | " |
| 247 | H | 3,5-dimethylpyrazol-1-yl | " | " |
| 248 | H | 4-methylpyrazol-1-yl | " | " |
| 249 | H | imidazol-1-yl | " | " |
| 250 | H | 1,2,3-triazol-1-yl | " | " |
| 251 | H | 3-methyl-1,2,4-triazol-1-yl | " | " |
| 252 | H | —N(piperazinyl)—N⁺(H)(CH₃)₂ CH₃SO₄⁻ | water | blue |

Table I-continued

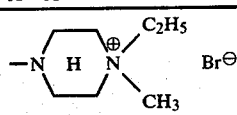

| Ex. | R¹ | X—A | Dissolved in | Shade of fluorescence |
|---|---|---|---|---|
| 253 | H | 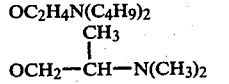 | " | " |
| 254 | $CH_3$ | $OC_2H_4N(CH_3)_2$ | dilute acid | bluish violet |
| 255 | " | $OC_2H_4N(C_3H_7)_2$ | " | " |
| 256 | $CH_3$ | $OC_3H_6N(C_2H_5)_2$ | " | " |
| 257 | $CH_3$ | $OC_2H_4N(C_4H_9)_2$ | " | " |
| 258 | $CH_3$ | $OCH_2-\overset{CH_3}{\underset{}{CH}}-N(CH_3)_2$ | " | " |
| 259 | $CH_3$ | 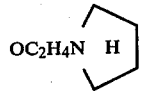 | " | " |
| 260 | $CH_3$ | 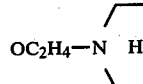 | " | " |
| 261 | $CH_3$ | 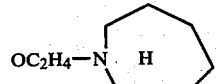 | " | " |
| 262 | $CH_3$ | 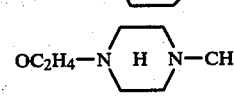 | " | " |
| 263 | $C_2H_5$ | $OC_2H_4N(CH_3)_2$ | " | " |
| 264 | $C_2H_5$ | $OC_3H_6N(CH_3)_2$ | " | " |
| 265 | $C_3H_6$ | $OC_2H_4N(CH_3)_2$ | " | " |
| 266 | $C_3H_6$ | $OC_3H_6N(CH_3)_2$ | " | " |
| 267 | $CH_3$ | 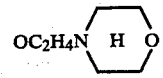 | " | " |
| 268 | $CH_3$ | $N(CH_3)_2$ | dimethylformamide | violet |
| 269 | $CH_3$ | $N(C_2H_5)_2$ | " | " |
| 270 | $CH_3$ | $N(C_4H_9)_2$ | " | " |
| 271 | $CH_3$ |  | " | " |
| 272 | $CH_3$ |  | " | " |
| 273 | $CH_3$ | 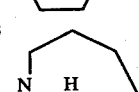 | " | " |
| 274 | $CH_3$ |  | " | " |
| 275 | $CH_3$ |  | " | " |
| 276 | $CH_3$ | $NH-C_2H_4N(CH_3)_2$ | dilute acid | bluish violet |
| 277 | $CH_3$ | $NH-C_3H_6-N(C_2H_5)_2$ | " | " |
| 278 | $CH_3$ | $NH-C_3H_6-N(C_4H_9)_2$ | " | " |
| 279 | $CH_3$ | $NH-\overset{CH_3}{\underset{}{CH}}-CH_2-N(C_4H_9)_2$ | " | " |

Table I-continued

Structure: 4-chlorophenyl-pyrazoline-N-phenyl-SO₂-CH₂-CH(CH₂R¹)(X-A)

| Ex. | R¹ | X—A | Dissolved in | Shade of fluorescence |
|---|---|---|---|---|
| 280 | CH₃ | NH—CH(C₂H₅)—CH₂—N(C₄H₉)₂ | " | " |
| 281 | CH₃ | NH—CH(C₂H₅)—CH₂—N(piperidine-H) | " | " |
| 282 | CH₃ | NH—CH(C₂H₅)—CH₂—N(hexamethyleneimine-H) | " | " |
| 283 | H | SCH₃ | dimethylformamide | violet |
| 284 | H | SC₂H₅ | " | " |
| 285 | H | SC₄H₉ | " | " |
| 286 | CH₃ | S—CH₂—CH=CH₂ | " | " |
| 287 | C₂H₅ | S—CH₂—C₆H₅ | " | " |
| 288 | H | S—CH₂COOH | dilute alkali | blue |
| 289 | H | SC₂H₄COOH | " | " |
| 290 | CH₃ | SC₂H₄COOH | " | " |
| 291 | CH₃ | OC₂H₄N⁺(CH₃)₃ CH₃SO₄⁻ | " | " |
| 292 | C₂H₅ | OC₃H₆N⁺(CH₃)₃ CH₃SO₄⁻ | " | " |
| 293 | CH₃ | OC₃H₆N⁺(CH₃)₃ ZnCl₃⁻ | " | " |
| 294 | CH₃ | OC₂H₄—N⁺(morpholine-CH₃) CH₃SO₄⁻ | " | " |
| 295 | CH₃ | OH | dimethylformamide | bluish violet |
| 296 | CH₃ | HN—C₆H₄—SO₃H | dilute alkali | blue |
| 297 | CH₃ | NH—CH₂CH₂SO₃H | " | " |
| 298 | CH₃ | O—CH₂CH₂SO₃H | " | " |
| 299 | H | OCH₂CH₂SO₃H | " | " |
| 300 | H | NH—C(O)—C₂H₄SO₃H | " | " |
| 301 | H | NH—C(O)—C₂H₅ | dimethylformamide | violet |
| 302 | H | NHC(O)—C₃H₇ | " | " |
| 303 | H | NH—C(O)—C₆H₅ | " | " |
| 304 | H | —N(CH₃)—C(O)—C₆H₅ | " | " |
| 305 | H | —N(CH₂C₆H₅)—C(O)—CH₃ | " | " |
| 306 | H | —N(CH₂C₆H₅)—SO₂—CH₃ | " | " |
| 307 | H | —NHSO₂—C₆H₅ | " | " |
| 308 | H | NHC(O)—C₆H₄—OCH₃ | " | " |
| 309 | H | NHC(O)—C₇H₁₅ | " | " |

Table I-continued

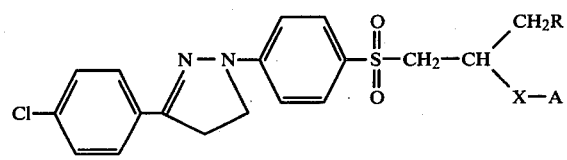

| Ex. | R¹ | X—A | Dissolved in | Shade of fluorescence |
|---|---|---|---|---|
| 310 | H | NH—C(=O)—$C_2H_4Cl$ | " | " |
| 311 | $CH_3$ | NH—C(=O)—$CH_3$ | " | " |
| 312 | $CH_3$ | NH—C(=O)—$C_2H_5$ | " | " |
| 313 | $CH_3$ | NHC(=O)—$C_6H_5$ | " | " |
| 314 | $CH_3$ | NH—C(=O)—$C_6H_4CH_3$ | " | " |
| 315 | $CH_3$ | NHC(=O)—$CH_2CH_2SO_3H$ | " | " |

EXAMPLE 316

12 parts of 1-(p-allylsulfonylphenyl)-3-(3',4'-dichlorophenyl)-Δ²-pyrazoline, 25 parts of N,N-diethylethanolamine and 0.5 part of 30% caustic soda solution are stirred for thirty minutes at 70° to 80° C.

After the whole has been cooled it is stirred into water and suction filtered. 15 parts of a compound of the following constitution is obtained:

The melting point is 154° to 155° C.

The reaction of 22 parts of p-allylsulfonylphenylhydrazine and 23 parts of 3,4-ω-trichloropropiophenone on 250 parts of methanol gives 29 parts of 1-(p-allylsulfonylphenyl)-3-(3,4-dichlorophenyl)-Δ²-pyrazoline. The melting point is 184° to 186° C.

EXAMPLE 317

10 parts of 1-(p-crotylsulfonylphenyl)-3-(3',4'-dichlorophenyl)-Δ²-pyrazoline and 25 parts of N,N-dimethylpropanolamine are heated to 90° to 100° C. 1 part of 50% caustic soda solution is added in three portions over a period of thirty minutes. The whole is stirred for another thirty minutes, allowed to cool, stirred into water and suction filtered. 12 parts of the following compound is obtained:

The 1-(p-crotylsulfonylphenyl)-3-(3',4'-dichlorophenyl)-Δ²-pyrazoline is obtained as follows:

14 parts of p-crotylsulfonylphenylhydrazine, 12 parts of 3,4-ω-trichloropropiophenone and 150 parts of methanol are stirred for four hours at 65° C. 18 parts of 1-(p-crotyl-sulfonylphenyl)-3-(3',4'-dichlorophenyl)-Δ²-pyrazoline crystallizes out overnight. The melting point is 170° to 171° C.

EXAMPLE 318

12 parts of 1-(p-allylsulfonylphenyl)-3-(3',4'-dichlorophenyl)-Δ²-pyrazoline and 20 parts of hexamethyleneimine are stirred for six hours at 100° C. The excess hexamethyleneimine is distilled off at subatmospheric pressure and the residue is taken up in methanol. 14 parts of the following compound is obtained:

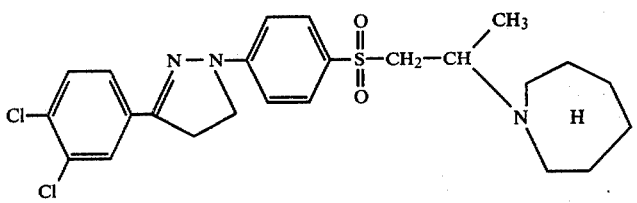

The melting point is 144° to 145° C.

EXAMPLE 319

12 parts of 1-(p-allylsulfonylphenyl)-3-(3',4'-dichlorophenyl)-Δ²-pyrazoline and 25 parts of methoxypropylamine are heated to 100° C. 0.3 part of 40% caustic potash solution is added and stirring is continued for two hours. After the whole has been cooled it is stirred into water, 14 parts of the following compound is obtained:

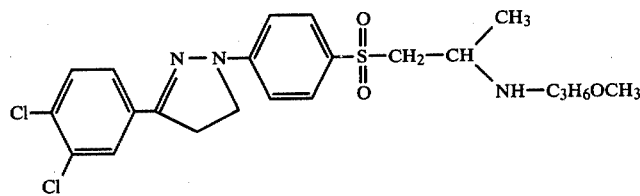

It has a melting point of 112° to 114° C.

The compounds set out in Tables I and II may also be prepared according to the following Examples.

EXAMPLE 320

20.3 parts of p-ω-dichloropropiophenone, 33 parts of p-(diethylaminoethyloxyisopropylsulfonyl)-phenylhydrazine and 300 parts of methanol are stirred for five hours at 65° C. and then allowed to cool. 30 parts of 1-[p-(diethylaminoethyloxyisopropylsulfonyl)-phenyl]-3-[p-chlorophenyl]-Δ²-pyrazoline is obtained. It has a melting point of 144° to 147° C.

p-(diethylaminoethyloxyisopropylsulfonyl)-phenylhydrazine may be prepared as follows:

35.8 parts of p-(diethylaminoethyloxyisopropylsulfonyl)-acetanilide, 80 parts of concentrated hydrochloric acid and 50 parts of water are stirred for sixty minutes at 90° to 100° C.

50 parts of ice is added. Diazotization is carried out at 0° to −5° C. with 7 parts of sodium nitrite dissolved in 15 parts of water. The diazonium salt solution is stirred at 0° to 5° C. into a solution of 65 parts of sodium sulfite and 280 parts of water. The whole is stirred for another hour. After cooling and adjusting the pH to 8 to 9 26 parts of p-(diethylaminoethyloxyisopropylsulfonyl)-phenylhydrazine is precipitated.

p-(diethylaminoethyloxyisopropylsulfonyl)-acetanilide is obtained in the following way:

2 parts of 50% caustic soda solution is dripped over two hours while stirring at 120° C. into 20 parts of p-allylsulfonylacetanilide and 25 parts of N,N-diethylethanolamine. The whole is stirred for another hour and then precipitation is effected with ice-water. 20 parts of p-(diethylaminoethyloxyisopropylsulfonyl)-acetanilide is obtained which does not crystallize well.

EXAMPLE 321

23.8 parts of 3,4-ω-trichloropropiophenone, 34.3 parts of p-(morpholinoethyloxyisopropylsulfonyl)-phenylhydrazine and 300 parts of methanol are stirred for five hours at 65° C. After cooling 1-[p-(morpholinoethyloxyisopropylsulfonyl)-phenyl]-3-(3',4'-dichlorophenyl)-Δ²-pyrazoline is obtained. It has a melting point of 153° to 154° C.

EXAMPLE 322

1-[p-(dimethylaminoethyloxyisopropylsulfonyl)-phenyl]-3-(3',4'-dichlorophenyl)-Δ²-pyrazoline having a melting point of 150° to 151° C. is obtained analogously to Example 321 using p-(dimethylaminoethyloxyisopropylsulfonyl)-phenylhydrazine.

EXAMPLE 323

1-[p-(dimethylaminopropyloxyisopropylsulfonyl)-phenyl]-3-(3',4'-dichlorophenyl)-Δ²-pyrazoline having a melting point of 140° to 142° C. is obtained analogously to Example 321 using p-(dimethylaminopropyloxyisopropylsulfonyl)-phenylhydrazine.

EXAMPLE 324

20.3 parts of p-ω-dichloropropiophenone, 30 parts of p-(morpholinoisopropylsulfonyl)-phenylhydrazine and 300 parts of methanol are stirred for five hours at 65° C. After cooling there is obtained 27 parts of 1- p-(morpholinoisopropylsulfonyl)-phenyl -3-(p-chlorophenyl)-Δ²-pyrazoline having a melting point of 157° to 169° C.

EXAMPLE 325

20.3 parts of p-ω-dichloropropiophenone, 28.5 parts of p-(butylaminoisopropylsulfonyl)-phenylhydrazine and 300 parts of methanol are stirred for five hours at 65° C. After cooling there is obtained 26 parts of 1-[p-(butylaminoisopropylsulfonyl)-phenyl]-3-(p-chlorophenyl)-Δ²-pyrazoline having a melting point of 112° to 114° C.

The compounds shown in Table II are obtained by methods analogous to those described in the Examples.

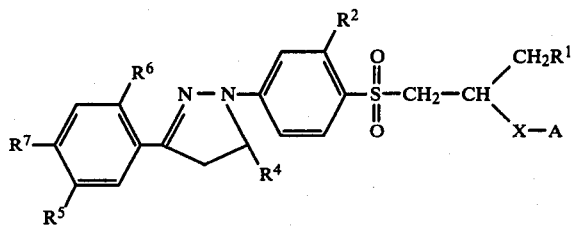

| Ex. | R¹ | R² | R⁴ | R⁵ | R⁶ | R⁷ | X-A | Dissolved in | Shade of fluorescence |
|---|---|---|---|---|---|---|---|---|---|
| 326 | H | CH₃ | CH₃ | H | H | Cl | OC₂H₄—N(CH₃)₂ | dilute acid | blue |
| 327 | H | H | C₂H₅ | Cl | H | H | OC₃H₆—N(CH₃)₂ | " | greyish blue |
| 328 | H | CH₃ | C₆H₅ | Cl | CH₃ | Cl | OC₂H₄N(CH₃)₂ | " | blue |
| 329 | H | H | H | Cl | CH₃ | Cl | OC₂H₄N(CH₃)₂ | " | " |
| 330 | H | H | H | Cl | CH₃ | Cl | OC₂H₄N⟨morpholine⟩ | " | " |
| 331 | H | H | H | Cl | CH₃ | Cl | NHC₂H₄N(CH₃)₂ | " | " |
| 332 | H | H | H | Cl | CH₃ | Cl | NH—CH(C₂H₅)—CH₂—N⟨piperidine⟩ | " | " |
| 333 | H | H | H | Cl | CH₃ | Cl | NH—CH(CH₃)—CH₂—N⟨piperidine⟩ | " | " |
| 334 | H | H | H | Cl | CH₃ | Cl | NH—C₃H₆—N⟨piperidine⟩ | " | " |
| 335 | H | H | H | Cl | CH₃ | Cl | SO₃H | dilute alkali | " |
| 336 | H | H | H | Cl | CH₃ | Cl | NH—C₂H₄—SO₃H | " | " |
| 337 | H | H | H | Cl | CH₃ | Cl | OC₂H₄SO₃H | " | " |
| 338 | H | H | H | Cl | CH₃ | Cl | OC₃H₆N(C₂H₅)₂ | dilute acid | " |
| 339 | H | H | H | Cl | CH₃ | Cl | OC₂H₄N⟨piperidine⟩ | " | " |
| 340 | H | H | H | Cl | CH₃ | Cl | OC₂H₄—N⟨hexamethyleneimine⟩ | " | " |
| 341 | H | Cl | H | Cl | H | Cl | OC₂H₄—N(CH₃)₂ | " | " |
| 342 | CH₃ | H | H | Cl | H | Cl | OC₂H₄—N⟨morpholine⟩ | " | " |
| 343 | CH₃ | H | H | Cl | H | Cl | OC₃H₆N(CH₃)₂ | " | greenish blue |
| 344 | CH₃ | Cl | H | H | H | OCH₃ | OC₃H₆N(CH₃)₂ | " | " |
| 345 | CH₃ | Cl | H | H | H | CH₃ | OC₂H₄N(CH₃)₂ | " | " |
| 346 | H | H | H | Cl | H | Cl | OC₃H₆N(C₃H₇)₂ | " | blue |
| 347 | H | H | H | Cl | H | Cl | OC₃H₆N(C₂H₅)₂ | " | " |
| 348 | H | H | H | Cl | H | Cl | OC₂H₄—N⟨pyrrolidine⟩ | " | " |
| 349 | H | H | H | Cl | H | Cl | OC₂H₄N⟨piperidine⟩ | " | " |

-continued

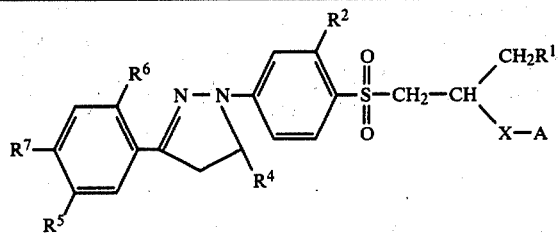

| Ex. | R¹ | R² | R⁴ | R⁵ | R⁶ | R⁷ | X-A | Dissolved in | Shade of fluorescence |
|---|---|---|---|---|---|---|---|---|---|
| 350 | H | H | H | Cl | H | Cl | OC₂H₄N⟨azepane⟩ | " | " |
| 351 | H | H | H | Cl | H | Cl | OC₃H₆—N⟨pyrrolidine⟩ | " | " |
| 352 | H | H | H | Cl | H | Cl | OC₃H₆—N⟨morpholine⟩ | " | " |
| 353 | H | H | H | Cl | H | Cl | N⟨morpholine⟩ | " | " |
| 354 | H | H | H | Cl | H | Cl | N⟨N-methylpiperazine⟩ | " | " |
| 355 | H | H | H | H | H | H | N⟨N-ethylpiperazine⟩ | " | greenish blue |
| 356 | H | H | H | H | H | CH₃ | OC₂H₄N(CH₃)₂ | " | " |
| 357 | H | H | H | H | H | C₂H₅ | OC₂H₄N(CH₃)₂ | " | " |
| 358 | H | H | C₆H₄CH₃ | H | H | Cl | OC₃H₆N(CH₃)₂ | " | blue |
| 359 | H | H | C₆H₄OCH₃ | H | H | Cl | OC₃H₆N(CH₃)₂ | " | " |
| 360 | H | H | C₆H₄N(CH₃)₂ | H | H | Cl | OC₂H₄N(CH₃)₂ | " | " |
| 361 | H | H | C₆H₄SO₃H | H | H | Cl | NHC₄H₉ | dilute alkali | " |
| 362 | H | H | C₆H₄SO₃H | H | H | Cl | NHC₆H₁₃ | " | " |
| 363 | H | H | C₆H₄SO₃H | H | H | Cl | NHC₃H₇ | " | " |

EXAMPLE 364

37.6 parts of 1-[4'-(β,γ-epoxypropylsulfonyl)-phenyl-]3-p-chlorophenylpyrazoline, 41 parts of 3-dimethylaminopropylamine and 2 parts of diaminocyclo-[2,2,2]-octane are stirred in 80 parts of dimethylformamide for three hours at 130° to 140° C. The whole is allowed to cool, precipitated with water and suction filtered. There is obtained a yield of 29 parts (60.4% of theory) of the compound:

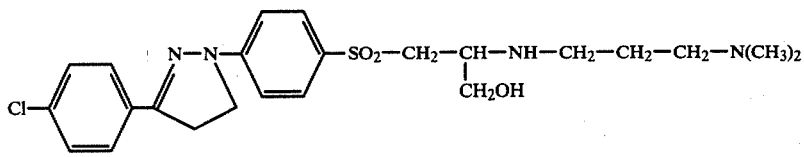

The product is pale yellow and exhibits an intensely blue fluorescence in solution.

EXAMPLE 365

103.3 parts of the compound from Example B(c) and 27 parts of sodium carbonate are dissolved in 300 parts of water and 300 parts of N-methylpyrrolidone and heated for three hours at 70° to 80° C. 126 parts of sodium sulfite is then added and the whole is heated for another three hours at 70° to 80° C. The whole is cooled to ambient temperature, suction filtered, dried and 114 parts of the following compound is isolated:

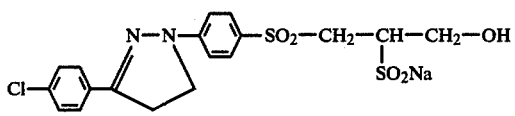

The product is pale yellow. A solution of the product in water has an intense blue fluorescence. NMR (D₆-DMSO): OH-signal as a triplet at 4.46 ppm.

EXAMPLE 366

94 parts of the compound from Example A(c) and 24 parts of ethanolamine are heated in 300 parts of methanol for five hours at 60° to 65° C. The whole is cooled to 0° to 5° C. and 86 parts of the following compound is isolated by suction filtration:

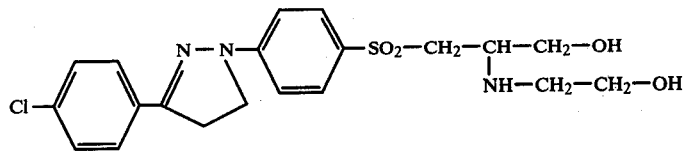

The melting point is 106° to 110° C.

The product is pale yellow and its solution in dimethylformamide has an intense blue fluorescence. (Absorption $\lambda_{max}$. 368 nm, Reflectance $\lambda_{max}$. 437.5 nm).

Compounds set out in the following Table are obtained analogously to Example 366:

| Ex. | $R_5$ | $R_6$ | XA | m.pt. | Fluorescence in dimethylformamide |
|---|---|---|---|---|---|
| 367 | H | H | $NHC_4H_9$ | 109–114 | blue |
| 368 | Cl | H | $SO_3Na$ | >300 | greenish blue |
| 369 | Cl | H | $NH(CH_2)_3N(CH_3)_2$ | 125–128 | greenish blue |
| 370 | Cl | $CH_3$ | (morpholino) | 195–200 | greenish blue |
| 371 | H | H | (N-methylpiperazino) | 205–210 | blue |
| 372 | H | H | $OCH_3$ | 120–125 | blue |

We claim:

1. A compound which in the form of the free acid corresponds to the formula

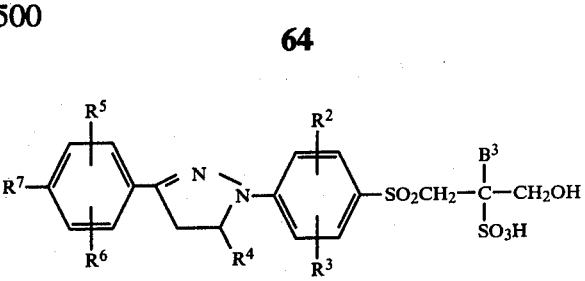

in which

B³ is hydrogen or $C_1$ to $C_4$ alkyl, $R^2$, $R^3$, $R^5$, $R^6$ and $R^7$ are independently hydrogen, chlorine, bromine, fluorine, methyl, ethyl, methoxy or ethoxy and $R^4$ is hydrogen, $C_1$ to $C_4$ alkyl, benzyl, phenylethyl, phenyl or phenyl substituted by chlorine, bromine, methyl, ethyl, methoxy, ethoxy, cyano or hydroxysulfonyl.

2. A compound according to claim 1 in which $R^2$, $R^3$, $R^4$, $R^5$, $R^6$ and $B^3$ are hydrogen.

3. A compound according to claim 2 in which $R^7$ is chlorine.